US008845741B2

(12) United States Patent
Boyden et al.

(10) Patent No.: US 8,845,741 B2
(45) Date of Patent: Sep. 30, 2014

(54) ARTIFICIAL JOINT COMPONENTS INCLUDING INTEGRAL MAGNETIC FIELDS CONFIGURED TO DEFLECT WEAR DEBRIS PARTICLES

(71) Applicant: Elwha LLC, Bellevue, WA (US)

(72) Inventors: Edward S. Boyden, Chestnut Hill, MA (US); Gregory J. Della Rocca, Columbia, MO (US); Daniel Hawkins, Bellevue, WA (US); Roderick A. Hyde, Redmond, WA (US); Robert Langer, Newton, MA (US); Eric C. Leuthardt, St. Louis, MO (US); Terence Myckatyn, St. Louis, MO (US); Parag Jitendra Parikh, St. Louis, MO (US); Dennis J. Rivet, Chesapeake, VA (US); Joshua S. Shimony, St. Louis, MO (US); Michael A. Smith, Phoenix, AZ (US); Clarence T. Tegreene, Mercer Island, WA (US)

(73) Assignee: Seavete LLC, Bellevue, WA (US)

( * ) Notice: Subject to any disclaimer, the term of this patent is extended or adjusted under 35 U.S.C. 154(b) by 31 days.

(21) Appl. No.: 13/675,068

(22) Filed: Nov. 13, 2012

(65) Prior Publication Data
US 2014/0088721 A1    Mar. 27, 2014

Related U.S. Application Data

(63) Continuation-in-part of application No. 13/628,442, filed on Sep. 27, 2012, and a continuation-in-part of
(Continued)

(51) Int. Cl.
*A61F 2/30* (2006.01)
*A61F 2/28* (2006.01)
*A61F 2/32* (2006.01)
*A61F 2/40* (2006.01)
*A61F 2/38* (2006.01)

(52) U.S. Cl.
CPC ... *A61F 2/30* (2013.01); *A61F 2/40* (2013.01); *A61F 2/38* (2013.01); *A61F 2/32* (2013.01)
USPC .................. 623/18.11; 623/16.11; 623/22.11; 623/19.11; 623/20.14

(58) Field of Classification Search
CPC .... A61F 2/28; A61F 2/38; A61F 2002/30079
USPC ........... 623/11.11, 16.11–19.13, 20.14, 22.11
See application file for complete search history.

(56) References Cited

U.S. PATENT DOCUMENTS

| 4,731,088 A | 3/1988 | Collier |
| 5,378,228 A | 1/1995 | Schmalzried et al. |

(Continued)

FOREIGN PATENT DOCUMENTS

| WO | WO 2008/044229 A1 | 4/2008 |
| WO | WO 2008/057565 A2 | 5/2008 |

OTHER PUBLICATIONS

Agarwal, Sanjeev; "Osteolysis—basic science, incidence and diagnosis"; Current Orthopaedics; 2004; pp. 220-231; vol. 18; Elsevier Ltd.

(Continued)

*Primary Examiner* — Jason-Dennis Stewart
(74) *Attorney, Agent, or Firm* — Advent, LLP

(57) ABSTRACT

Prosthetic artificial joints are described, including hip, knee and shoulder joints. In some embodiments, an artificial joint prosthesis includes: a bone-facing surface of a artificial joint prosthesis, the bone-facing surface configured to face a bone-prosthesis interface in vivo; a first component of the artificial joint prosthesis including a contact surface of the artificial joint prosthesis, the first component fabricated from at least one polymer and a plurality of magnetic particles; and a second component of the artificial joint prosthesis including at least one magnet configured to create a magnetic field within the artificial joint, the at least one magnet positioned to form a magnetic field directed to influence a location of debris including the magnetic particles in the joint to a position distinct from the bone-prosthesis interface in vivo.

35 Claims, 11 Drawing Sheets

Related U.S. Application Data application No. 13/629,918, filed on Sep. 28, 2012, and a continuation-in-part of application No. 13/658,982, filed on Oct. 24, 2012, and a continuation-in-part of application No. 13/659,020, filed on Oct. 24, 2012.

(56) References Cited

U.S. PATENT DOCUMENTS

| | | | |
|---|---|---|---|
| 5,514,182 A | 5/1996 | Shea | |
| 5,558,091 A | 9/1996 | Acker et al. | |
| 5,571,195 A | 11/1996 | Johnson | |
| 5,665,118 A | 9/1997 | LaSalle et al. | |
| 5,769,093 A | 6/1998 | Bays | |
| 5,879,404 A | 3/1999 | Bateman et al. | |
| 5,879,406 A | 3/1999 | Lilley | |
| 5,916,269 A | 6/1999 | Serbousek et al. | |
| 6,132,470 A | 10/2000 | Berman | |
| 6,368,354 B2 | 4/2002 | Burstein et al. | |
| 6,432,141 B1 | 8/2002 | Stocks et al. | |
| 6,569,202 B2 | 5/2003 | Whiteside | |
| 6,599,321 B2 | 7/2003 | Hyde, Jr. | |
| 6,761,741 B2 | 7/2004 | Iesaka | |
| 7,144,427 B2 | 12/2006 | Southworth | |
| 7,476,250 B1 | 1/2009 | Mansmann | |
| 7,758,653 B2 | 7/2010 | Steinberg | |
| 7,811,328 B2 | 10/2010 | Molz, IV et al. | |
| 2002/0087213 A1* | 7/2002 | Bertram, III | 623/18.12 |
| 2003/0014122 A1 | 1/2003 | Whiteside | |
| 2003/0130740 A1 | 7/2003 | Stocks et al. | |
| 2003/0195633 A1 | 10/2003 | Hyde, Jr. | |
| 2003/0229398 A1 | 12/2003 | Iesaka | |
| 2003/0233149 A1 | 12/2003 | Hodorek | |
| 2004/0068322 A1 | 4/2004 | Ferree | |
| 2004/0111162 A1 | 6/2004 | Southworth | |
| 2005/0055101 A1 | 3/2005 | Sifneos | |
| 2005/0075719 A1 | 4/2005 | Bergheim | |
| 2006/0149386 A1 | 7/2006 | Clarke et al. | |
| 2008/0306324 A1 | 12/2008 | Bonutti et al. | |
| 2009/0005867 A1 | 1/2009 | Lefranc et al. | |
| 2010/0145464 A1* | 6/2010 | Sidhom | 623/18.12 |
| 2010/0222890 A1 | 9/2010 | Barnett et al. | |
| 2010/0262160 A1 | 10/2010 | Boyden et al. | |
| 2011/0116968 A1 | 5/2011 | Brunner et al. | |
| 2012/0150310 A1 | 6/2012 | Taylor et al. | |
| 2012/0191202 A1 | 7/2012 | Borowsky | |

OTHER PUBLICATIONS

Anthony et al.; "Localised Endosteal Bone Lysis in Relation to the Femoral Components of Cemented Total Hip Arthroplasties"; The Journal of Bone and Joint Surgery; Nov. 1990; pp. 971-979; vol. 72-B, No. 6; British Editorial Society of Bone and Joint Surgery.

Bartlett et al.; "In vitro influence of stem surface finish and mantle conformity on pressure generation in cemented hip arthroplasty"; Acta Orthopaedica; 2009; pp. 139-143; vol. 80, No. 2; Informa Healthcare Ltd.

Bartlett et al.; "The femoral stem pump in cemented hip arthroplasty: An in vitro model"; Medical Engineering and Physics; 2008; pp. 1042-1048; vol. 30; Elsevier Ltd.

Bhattacharya et al.; "Propulsion and Trapping of Microparticles by Active Cilia Arrays"; Langmuir; 2012; pp. 3217-3226; vol. 28; American Chemical Society.

Chatterjee et al.; "Synthesis of Polyethylene Magnetic Nanoparticles"; European Cells and Materials; 2002; pp. 98-101; vol. 3, Suppl. 2.

Collier et al.; "Osteolysis After Total Knee Arthroplasty: Influence of Tibial Baseplate Surface Finish and Sterilization of Polyethylene Insert, Findings at Five to Ten Years Postoperatively"; The Journal of Bone and Joint Surgery; Dec. 2005; pp. 2702-2708; vol. 87-A, No. 12.

Fahlgren et al.; "Fluid pressure and flow as a cause of bone resorption"; Acta Orthopaedica; 2010; pp. 508-516; vol. 81, No. 4.

Keawboonchuay et al.; "Maximum Power Generation in a Piezoelectric Pulse Generator"; IEEE Transactions on Plasma Science; Feb. 2003; pp. 123-128; vol. 31, No. 1; IEEE.

Killeya, Matthew; "First practical plastic magnets created"; New Scientist; Aug. 30, 2004; pp. 1-3.

Linden, Joel; "Longer life for artificial joints"; Nature; Jul. 12, 2012; pp. 179-180; vol. 487; Macmillan Publishers Limited.

Manley et al.; "Osteolysis: A Disease of Access to Fixation Interfaces"; Clinical Orthopaedics and Related Research; 2002; pp. 129-137; No. 405; Lippincott Williams & Wilkins, Inc.

Mediero et al.; "Adenosine $A_{2A}$ Receptor Activation Prevents Wear Particle-Induced Osteolysis"; Science Translational Medicine; May 23, 2012; pp. 1-10 plus cover page; vol. 4, 135ra65; American Association for the Advancement of Science.

Millan et al.; "Magnetic polymer nanocomposites"; Chapter 17 in Polymer Nanocomposites, Mai and Yu, eds.; 2006; pp. 440-484 and two cover pages; CRC Press, Woodhead Publishing Limited.

Smith et al.; "Failure rates of stemmed metal-on-metal hip replacements: analysis of data from the National Joint Registry of England and Wales"; The Lancet; Mar. 31, 2012; pp. 1199-1204; vol. 379.

Van Engen, Willem; "Artificial cilia for microfluidics exploring the use of a horizontally micro-structured ferromagnetic PDMS composite"; Master's Thesis, Eindhoven University of Technology; 2008; pp. 1-70; Eindhoven, Netherlands.

Wang et al.; "Novel magnetic polyethylene nanocomposites produced by supported nanometre magnetic Ziegler-Natta catalyst"; Polymer International; 2000; pp. 184-188; vol. 49; Society of Chemical Industry.

Xie, Jing; "A Systematic Review on Performance of the Vanguard® Complete Knee System"; Form No. BOI0500.0, REV083111; Jun. 30, 2011; pp. 1-11 and one additional page; Biomet Inc., Warsaw, Indiana.

U.S. Appl. No. 13/659,020, Boyden et al.
U.S. Appl. No. 13/658,982, Boyden et al.
U.S. Appl. No. 13/629,918, Boyden et al.
U.S. Appl. No. 13/628,442, Boyden et al.
PCT International Search Report; International Application No. PCT/US13/60577; Dec. 12, 2013; pp. 1-2.
PCT International Search Report; International App. No. PCT/US13/60573; Feb. 5, 2014; pp. 1-4.
PCT International Search Report; International App. No. PCT/US13/60568; Feb. 5, 2014; pp. 1-4.

* cited by examiner

ARTIFICIAL JOINT COMPONENTS INCLUDING INTEGRAL MAGNETIC FIELDS CONFIGURED TO DEFLECT WEAR DEBRIS PARTICLES If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application is related to and/or claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)). In addition, the present application is related to the "Related Applications," if any, listed below.

PRIORITY APPLICATIONS

For purposes of the USPTO extra-statutory requirements, the present application constitutes a continuation-in-part of U.S. patent application Ser. No. 13/628,442, entitled ARTIFICIAL JOINT COMPONENTS INCLUDING SYNOVIAL FLUID DEFLECTING STRUCTURES, naming Edward S. Boyden; Gregory J. Della Rocca; Daniel Hawkins; Roderick A. Hyde; Robert Langer; Eric C. Leuthardt; Terence Myckatyn; Parag Jitendra Parikh; Dennis J. Rivet; Joshua S. Shimony; Michael A. Smith; and Clarence T. Tegreene as inventors, filed 27 Sep. 2012, which is currently co-pending.

For purposes of the USPTO extra-statutory requirements, the present application constitutes a continuation-in-part of U.S. patent application Ser. No. 13/629,918, entitled ARTIFICIAL JOINT COMPONENTS INCLUDING SYNOVIAL FLUID DEFLECTING STRUCTURES AND PARTICLE RETAINING STRUCTURES, naming Edward S. Boyden; Gregory J. Della Rocca; Daniel Hawkins; Roderick A. Hyde; Robert langer; Eric C. Leuthardt; Terence Myckatyn; Parag Jitendra Parikh; Dennis J. Rivet; Joshua S. Shimony; Michael A. Smith; and Clarence T. Tegreene as inventors, filed 28 Sep. 2012, which is currently co-pending.

For purposes of the USPTO extra-statutory requirements, the present application constitutes a continuation-in-part of U.S. patent application Ser. No. 13/658,982, entitled ARTIFICIAL JOINT COMPONENTS INCLUDING MECHANIZED SYNOVIAL FLUID DEFLECTING STRUCTURES, naming Edward S. Boyden; Gregory J. Della Rocca; Daniel Hawkins; Roderick A. Hyde; Robert Langer; Eric C. Leuthardt; Terence Myckatyn; Parag Jitendra Parikh; Dennis J. Rivet; Joshua S. Shimony; Michael A. Smith; and Clarence T. Tegreene as inventors, filed 24 Oct. 2012, which is currently co-pending.

For purposes of the USPTO extra-statutory requirements, the present application constitutes a continuation-in-part of U.S. patent application Ser. No. 13/659,020, entitled ARTIFICIAL JOINT COMPONENTS INCLUDING MECHANIZED SYNOVIAL FLUID DEFLECTING STRUCTURES AND PARTICLE RETAINING 24 Oct. 2012, which is currently co-pending.

RELATED APPLICATIONS

None.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, Benefit of Prior-Filed Application, USPTO Official Gazette Mar. 18, 2003. The USPTO further has provided forms for the Application Data Sheet which allow automatic loading of bibliographic data but which require identification of each application as a continuation, continuation-in-part, or divisional of a parent application. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above and in any ADS filed in this application, but expressly points out that such designation(s) are not to be construed in any way as any type of commentary and/or admission as to whether or not the present application contains any new matter in addition to the matter of its parent application(s).

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

SUMMARY

In some embodiments, an artificial joint prosthesis includes, but is not limited to: a bone-facing surface of a artificial joint prosthesis, the bone-facing surface configured to face a bone-prosthesis interface in vivo; a first structural component of the artificial joint prosthesis including a load-bearing surface of the artificial joint prosthesis, the first component fabricated from at least one polymer and a plurality of magnetic particles; and a second structural component of the artificial joint prosthesis including at least one magnet configured to create a magnetic field within the artificial joint, the at least one magnet positioned to form a magnetic field directed to influence a location of debris including the magnetic particles in the joint to a position distinct from the bone-prosthesis interface in vivo.

In some embodiments, an artificial joint prosthesis includes, but is not limited to: a bone-facing surface of a artificial joint prosthesis, the bone-facing surface configured to face a bone-prosthesis interface in vivo; a first component of the artificial joint prosthesis including a contact surface of the artificial joint prosthesis, the first component fabricated from at least one polymer and a plurality of magnetic particles; and a second component of the artificial joint prosthesis including at least one magnet configured to create a magnetic field within the artificial joint, the at least one magnet positioned to form a magnetic field directed to influence a location of debris including the magnetic particles in the joint to a position distinct from the bone-prosthesis interface in vivo.

In some embodiments, an artificial hip joint prosthesis includes, but is not limited to: a bone-facing surface of an artificial hip joint prosthesis, the bone-facing surface configured to face a bone-prosthesis interface in vivo; a first component of the artificial hip joint prosthesis including a contact surface of the artificial hip joint prosthesis, the first component fabricated from at least one polymer and a plurality of magnetic particles; and a second component of the artificial hip joint prosthesis including at least one magnet configured to create a magnetic field within the artificial hip joint, the at least one magnet positioned to form a magnetic field directed to influence a location of debris including the magnetic particles in the joint to a position distinct from the bone-prosthesis interface in vivo.

In some embodiments, an artificial knee joint prosthesis includes, but is not limited to: a bone-facing surface of an artificial knee joint prosthesis, the bone-facing surface configured to face a bone-prosthesis interface in vivo; a first component of the artificial knee joint prosthesis including a contact surface of the artificial knee joint prosthesis, the first component fabricated from at least one polymer and a plurality of magnetic particles; and a second component of the artificial knee joint prosthesis including at least one magnet configured to create a magnetic field within the artificial knee joint, the at least one magnet positioned to form a magnetic field directed to influence a location of debris including the magnetic particles in the joint to a position distinct from the bone-prosthesis interface in vivo.

In some embodiments, an artificial shoulder joint prosthesis includes, but is not limited to: a bone-facing surface of an artificial shoulder joint prosthesis, the bone-facing surface configured to face a bone-prosthesis interface in vivo; a first component of the artificial shoulder joint prosthesis including a contact surface of the artificial shoulder joint prosthesis, the first component fabricated from at least one polymer and a plurality of magnetic particles; and a second component of the artificial shoulder joint prosthesis including at least one magnet configured to create a magnetic field within the artificial shoulder joint, the at least one magnet positioned to form a magnetic field directed to influence a location of debris including the magnetic particles in the joint to a position distinct from the bone-prosthesis interface in vivo.

In addition to the foregoing, other aspects of the artificial joint prostheses are described in the claims, drawings, and text forming a part of the disclosure set forth herein. The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
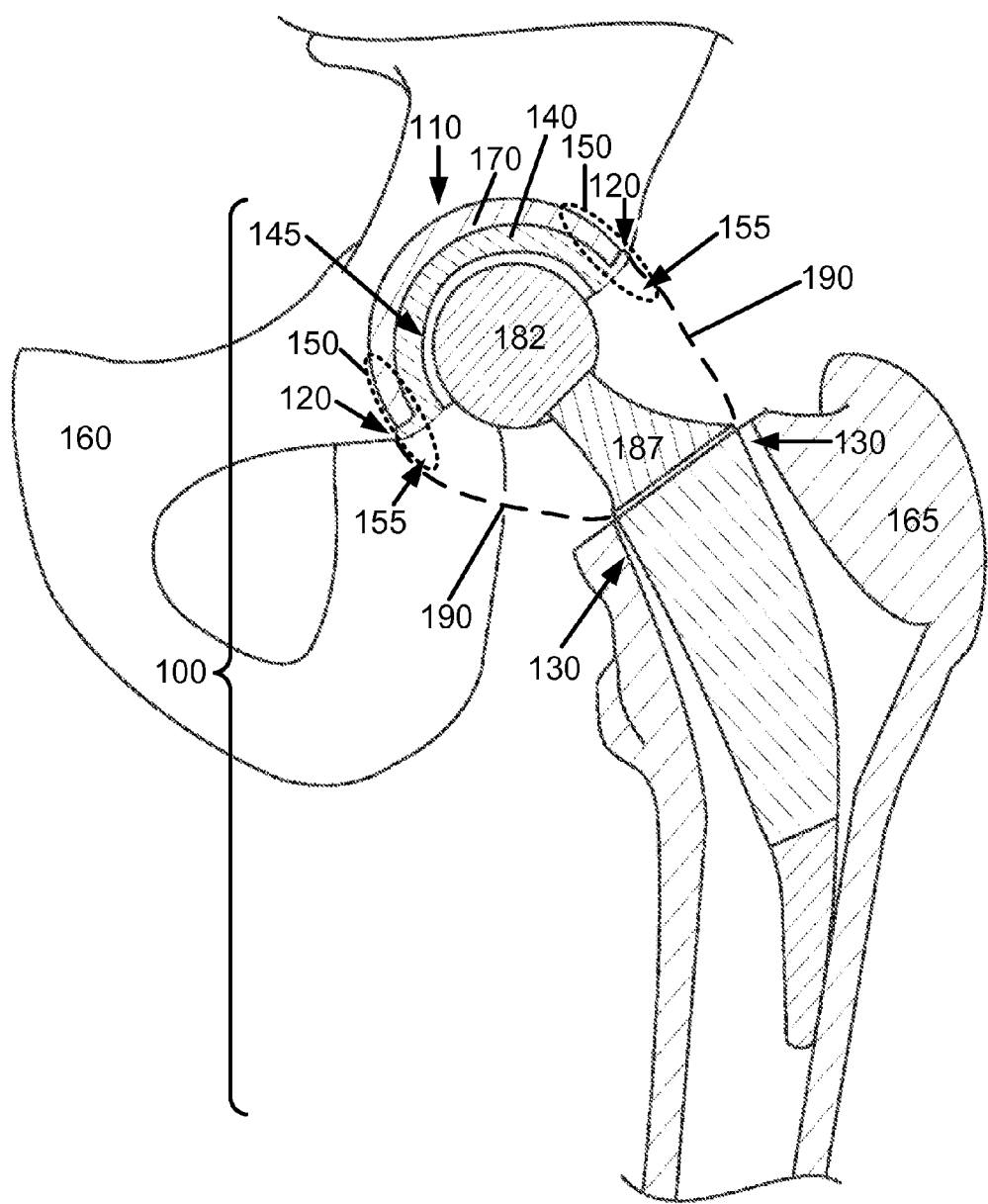
FIG. 1 illustrates a artificial hip joint in cross-section.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Artificial joint prostheses are used as a surgical therapeutic substitute for joint components that are damaged, such as due to injury or osteoarthritis. The goals of surgical implantation of artificial joint prostheses generally include improving joint function and alleviating pain. Although these surgeries have a high success rate, there is some risk over time that an artificial joint prosthesis can fail. Failure of artificial prosthetic joints can require further surgery, with associated costs and morbidity for the patient. One clinically significant type of artificial joint failure is associated with loosening of the prosthesis at the bone interface, including osteolysis and related damage to the bone.

Artificial joint prosthesis failure related to loosening of the prosthesis at the bone interface can have significant adverse clinical consequences. Patients can experience pain and reduced mobility, for example, which can pose a problem for patients who are otherwise active. In addition, artificial joint prosthesis failure related to loosening of the prosthesis can pose a particular problem in younger patients who have many years of expected lifespan ahead of them, with the associated need to preserve bone mass and joint function for the future. The negative consequences of prosthesis failure related to loosening of the prosthesis can also increase the medical burden of patients with secondary medical problems. For example, reduced mobility from prosthetic joint failure can be a significant problem for a person who uses exercise to control their high blood pressure. In some cases, surgical revision is required to address prosthesis failure related to loosening of the prosthesis, with associated costs and morbidity to the patient. Although surgical revision rates vary by the type of prosthesis used and patient subgroup, a recent study of hip prosthesis failure rates found 5 year revision rates ranging from 1.6% to 6.1% (Smith et al., "Failure rates of Stemmed Metal-on-metal Hip Replacements: Analysis of Data from the National Joint Registry of England and Wales," *The Lancet,* 379:1199-1204 (2012), which is incorporated herein by reference).

Artificial joint prosthesis failure is associated in a significant number of cases with loosening of the prosthesis at the prosthesis-joint interface or in the periprosthetic region due to loss of the adjacent bone. This is believed to be caused in part from osteolysis promoted by the body's response to debris from the artificial joint prosthesis. See, e.g. Linden, "Longer Life for Artificial Joints," Nature 487: 179-180, (2012): and U.S. Pat. No. 5,378,228 "Method and Apparatus for Joint Fluid Decompression and Filtration with Particulate Debris Collection," to Schmalzried and Jasty, which are each incorporated herein by reference. Wear debris from the prosthesis surface coming into contact with the bone-prosthesis interface has been implicated, for example, in loosening of the prosthesis and associated failure. Debris particles at the prosthesis-bone interface can contribute to osteolysis and resulting prosthesis loosening with potential failure of the prosthesis. Debris particles within the synovial fluid can include, for example, one or more of: cellular debris particles, particulates of bone and prosthesis generated during surgery, and particulates formed from wear of the artificial joint prosthesis. Some studies indicate that debris particles can enter the prosthesis-bone interface region through increased synovial fluid pressure at the prosthesis-joint interface during physiological movement. Some studies indicate that debris particles can enter the prosthesis-bone interface region through increased synovial fluid flow rate against the prosthesis joint interface during physiological movement. Studies also indicate that both fluid pressure and flow rate at the prosthesis-joint interface due to prosthesis movement during physiological activities encourage debris particles to enter the prosthesis-bone interface, contributing to osteolysis and prosthesis failure. See: Smith et al., ibid.; Fahlgren et al., "Fluid Pressure and Flow as a Cause of Bone Resorption," *Acta Orthopaedica* 81(4):508-516 (2010): Bartlett et al., "In Vitro Influence of Stem Surface Finish and Mantle Conformity on Pressure Generation in Cemented Hip Arthroplasty," *Acta Orthopaedica* 80(2): 139-143 (2009): Bartlett et al., "The Femoral Stem Pump in Cemented Hip Arthroplasty: an In Vitro Model," *Medical Engineering and Physics,* 30: 1042-1048 (2008): Agarwal, "Osteolysis—Basic Science, Incidence and Diagnosis," *Current Orthopaedics* 18: 220-231 (2004); Manley et al., "Osteolysis: a Disease of Access to Fixation Interfaces," Clinical Orthopaedics and Related Research 405:129-137 (2002); and Anthony et al., "Localized Endosteal Bone Lysis in Relation to the Femoral Components of Cemented Total Hip Arthroplasties," *British Journal of Bone and Joint Surgery,* 72-B(6): 971-979 (1990), which are each incorporated herein by reference. See also: US Patent Application No. 2003/0014122 and U.S. Pat. No. 6,569,202, each titled "Tray and Liner for Joint Replacement System," to Whiteside; US Patent Application No. 2005/0055101 "Endoprosthesis of the Knee and/or other Joints," to Sifneos; and US Patent Application No. 2004/0068322, "Reduced-Friction Artificial Joints and Components Therefor" to Ferree, which are each incorporated herein by reference.

The artificial joints described herein each include at least one component fabricated from at least one polymer and a plurality of magnetic particles. The at least one component fabricated from at least one polymer and a plurality of magnetic particles includes a surface subject to wear during physiological use of the joint, which can be described as a contact surface or a weight-bearing surface, for example. The magnetic particles within the polymer are dispersed within the polymer structure at a density sufficient to expect that each fragment of the polymer formed from wear during physiological use of the joint will include at least one of the magnetic particles. The polymer fragments, therefore, are expected to have magnetic properties as a consequence of the inclusion of the magnetic particles within the polymer structure.

The artificial joints described herein each include at least one component that includes at least one magnet configured to create a magnetic field within the joint, the magnetic field directed to influence a location of debris including the magnetic particles in the joint to a position distinct from the bone-prosthesis interface in vivo. The fragments, therefore, of the polymer will be influenced by the magnetic field to a location within the joint that is distinct from the bone-prosthesis interface in vivo. The minimization of wear particle debris at the bone-prosthesis interface in vivo will reduce the possibility of osteolysis at the bone interface, reducing the incidence of prosthesis failure. In addition, any debris particles that include physiological components, such as antibodies or macrophages, will also include the magnetic particles and be influenced by the magnetic field. For example, a macrophage that has engulfed any fragments including magnetic particles would be influenced by the magnetic field within the joint.

Artificial joints that are suitable for some embodiments described herein include: a hip joint prosthesis, a knee joint prosthesis, a shoulder joint prosthesis, an ankle joint prosthesis, or an elbow joint prosthesis. Although the artificial joint prostheses are described herein primarily in reference to humans, in some embodiments the artificial joint prostheses as described herein will also have applicability in veterinary medicine. For example, aspects of the artificial hip joint prosthesis as described herein (see, e.g. FIGS. 1-4 and associated text) have applicability in hip joint replacements in domestic animals, such as dogs and cats.

The artificial joint prosthesis components described herein include at least one component with a bone-facing surface of the artificial joint prosthesis, the bone-facing surface configured to face a bone-prosthesis interface in vivo. For example, the bone-facing surface of a component of the artificial joint can include: a region of a shell of a acetabular component of a hip joint prosthesis; a region of a liner of a acetabular component of a hip joint prosthesis; a region of a stem of a femoral component of a hip joint prosthesis; a region of a femoral component of a knee joint prosthesis; a region of a tibial component of a knee joint prosthesis; a region of a humeral stem of a shoulder joint prosthesis; a region of a humeral component of a shoulder joint prosthesis; or a region of a glenoid component to a scapula of a shoulder joint prosthesis.

The artificial joint prosthesis components described herein include at least one component with a contact surface, wherein the component is fabricated from at least one polymer integrating a plurality of magnetic particles. For example, in some embodiments, the component fabricated from at least one polymer integrating a plurality of magnetic particles can include: an acetabular component of a hip joint prosthesis; a head of a femoral component of a hip joint prosthesis; a femoral component of a knee joint prosthesis; a tibial component of a knee joint prosthesis; a patellar component of a knee joint prosthesis; a humeral component of a shoulder joint prosthesis; or a glenoid component to a scapula of a shoulder joint prosthesis. In some embodiments, the component is fabricated from a polymer including the plurality of magnetic particles embedded in a polymer matrix. In some embodiments, the component is fabricated from polyethylene including the plurality of magnetic particles embedded in a polymer matrix. In some embodiments, the component is fabricated from at least one magnetic polymer nanocomposite material. In some embodiments, the plurality of magnetic particles include magnetic nanoparticles, which are magnetic particles sized between approximately 100 nanometers (nm) in diameter and approximately 1 nanometer (nm) in diameter. In some embodiments, the component is fabricated from a polymer including a plurality of magnetic nanoparticles at an average density no less than 10 magnetic nanoparticles per square micron ($\mu m^2$) of the polymer. In some embodiments, the component is fabricated from a polymer including a plurality of magnetic nanoparticles at an average density no less than 100 magnetic nanoparticles per square micron ($\mu m^2$) of the polymer. In some embodiments, the plurality of magnetic particles include ferromagnetic particles. In some embodiments, the plurality of magnetic particles include paramagnetic particles. The polymer integrating a plurality of magnetic particles can include polyethylene magnetic particles. In some embodiments, the polymer integrating a plurality of magnetic particles can include polyethylene magnetic nanoparticles. The magnetic particles can be integrated into a polymer during fabrication of the artificial joint component. See: Chatterjee et al., "Synthesis of Polyethylene Magnetic Nanoparticles," *European Cells and Materials* 3(2): 98-101 (2002); Wang et al., "Novel Magnetic Polyethylene Nanocomposites Produced by Supported Nanometer Magentic Ziegler-Natta Catalyst," Polymer International 49: 184-188 (2000); Millan et al., "Magnetic Polymer Nanocomposites," chapter 17 in Polymer Nanocomposites, Mai and Yu, eds. CRC Press, 2006; and Killeya, "First Plastic Magnets Created," *New Scientist* (30 Aug. 2004), which are each incorporated herein by reference. The polymer integrating a plurality of magnetic particles can include ultra-high-molecular weight polyethylene (UHMWPE). The polymer integrating a plurality of magnetic particles can include highly cross-linked UHMWPE. See U.S. Patent Application Publication No. 2011/0116968 "Oxidation Resistant Highly-Crosslinked UHMWPE" to Brunner et al., which is incorporated by reference herein.

The "contact surface" of the artificial joint component, as used herein, refers to a surface of a component that is expected to come into contact with another component of the joint during normal physiological use of the artificial joint in vivo. For example, a contact surface can include a joint-facing surface of a acetabular liner of a hip joint, a joint-facing surface of a head of a femoral component of a knee joint, or a joint facing surface of a glenoid component to a scapula of a shoulder joint prosthesis. A component including a load-bearing surface is a structural component of the artificial joint during expected physiological use of the joint. As used herein, a "non-contact surface" of an artificial joint prosthesis refers to a surface of a component of the artificial joint prosthesis that is expected to not come into contact with the bone and also to not come into contact with a surface of another component of the artificial joint prosthesis during normal physiological use of the artificial joint prosthesis in vivo. In some instances, a contact surface of an artificial joint can be a "load bearing surface," or a surface of a joint component that is expected to come into contact with another component and to partially support the mass of the individual user during normal physiological use of the artificial joint in vivo. A component including a load-bearing surface is a structural component of the artificial joint during expected physiological use of the joint in vivo.

In some embodiments, a contact surface of an artificial joint component includes one or more indentations at the contact surface. These indentations can be formed as lines, channels or patterns at the contact surface. A contact surface of an artificial joint component can include, for example, one or more grooves in the contact surface. The indentations or grooves in the contact surface are configured to provide a space for wear debris from the artificial joint to accumulate away from a direct contact area of the contact surface. For example, the artificial joint can include a second component of the artificial joint prosthesis including at least one magnet configured to create a magnetic field within the artificial joint, the at least one magnet positioned to form a magnetic field directed to influence a location of debris including the magnetic particles in the joint to a position distinct from the bone-prosthesis interface in vivo, wherein the location is within the indentations or grooves in the contact surface. The indentations or grooves in the contact surface are configured to maintain the structural integrity of the component as a whole. See, for example, U.S. Pat. No. 5,916,269 "Wear Reduced Acetabular Component," to Serbousek and Bono, which is incorporated by reference herein.

The artificial joints also include a component which includes at least one magnet configured to create a magnetic field within the artificial joint, the at least one magnet positioned to form a magnetic field directed to influence a location of debris including the magnetic particles in the joint to a position distinct from the bone-prosthesis interface in vivo. For example, in some embodiments, the component including at least one magnet configured to create a magnetic field within the artificial joint includes at least one of: an acetabular liner of a hip joint prosthesis; a stem of a femoral component of a hip joint prosthesis; a femoral liner of a knee joint prosthesis; a tibial liner of a knee joint prosthesis; a patellar component of a knee joint prosthesis; a humeral component of a shoulder joint prosthesis; or a glenoid liner of a shoulder joint prosthesis. The component which includes at least one magnet configured to create a magnetic field within the artificial joint can be positioned adjacent to the component of the artificial joint prosthesis including a contact surface of the artificial joint prosthesis. For example, in some embodiments the component which includes at least one magnet is an acetabular shell or cup of an artificial hip joint, and the component of the artificial hip joint including a contact surface of the artificial joint prosthesis is an acetabular liner, which comes into contact with the femoral ball during expected physiological use of the artificial joint. For example, in some embodiments the component which includes at least one magnet is glenoid shell or cup to a scapula of an artificial shoulder joint, and the component of the artificial shoulder joint including a contact surface of the artificial joint prosthesis is an glenoid liner, which comes into contact with the humeral component during expected physiological use of the artificial joint. The component which includes at least one magnet configured to create a magnetic field within the artificial joint can be positioned distal to the component of the artificial joint prosthesis including a contact surface of the artificial joint prosthesis. For example, in some embodiments the component which includes at least one magnet is a tibial plate of an artificial knee joint, and the component of the artificial knee joint including a contact surface of the artificial joint prosthesis is an femoral component, which comes into contact with a tibial component during expected physiological use of the artificial joint.

In some embodiments, the component which includes at least one magnet includes an array of magnets configured as cooperating arrays to form a magnetic field, the magnetic field directed to influence a location of debris including any potential magnetic debris particles in the joint to a position distinct from the bone-prosthesis interface in vivo. See, for example, U.S. Pat. No. 6,599,321, "Magnetic Array Implant and Prosthesis," to Hyde, which is incorporated herein by reference. In some embodiments, the component which includes at least one magnet includes an array of magnets configured to operate as cooperating arrays with field characteristics predicted to influence a location of debris including any potential magnetic debris particles in the joint to a position distinct from the bone-prosthesis interface in vivo.

See, for example, U.S. Patent Application Publication No. 2003/0195633, "Magnetic Array Implant and Prosthesis Insert" to Hyde, which is incorporated herein by reference. In some embodiments, the component which includes at least one magnet is configured to generate a magnetic field that is predicted to repulse debris particles including magnetic particles away from the bone-prosthesis interface in vivo. See, for example, U.S. Pat. No. 7,811,328, "System, Device, and Methods for Replacing the Intervertebral Disk with a Magnetic or Electromagnetic Prosthesis, to Molz et al., which is incorporated by reference herein. In some embodiments, the component which includes at least one magnet is configured to generate a magnetic field that is predicted to attract magnetic debris particles to a location in the joint distal to the bone-prosthesis interface in vivo. In some embodiments, the component including at least one magnet configured to create a magnetic field within the artificial joint includes at least one permanent magnet. In some embodiments, the component including at least one magnet configured to create a magnetic field within the artificial joint includes at least one electromagnet. For example, the component can include at least one alternating current (AC) electromagnet. For example, the component can include at least one direct current (DC) electromagnet. In embodiments including electromagnets, the magnetic field of the joint can be periodically enhanced or supplanted through external energy transfer to the electromagnet.

In some embodiments, the component including at least one magnet configured to create a magnetic field within the artificial joint includes wherein the magnetic field is configured to retain the debris or wear fragments including the magnetic particles in a location adjacent to a surface of the component. For example, the magnetic field can be configured to attract the magnetic particles to a region of the interior of the joint that is adjacent to a surface of an artificial component, but distal to the bone-prosthesis interface. For example, the magnetic field can be configured to attract the magnetic particles to a surface of a joint component that is indented, so that the wear fragments and/or debris particles containing the wear fragments tend to accumulate in the indentation. For example, the artificial component can include indentations, grooves, notches or similar forms that create space adjacent to the surface of the joint component for the accumulation of wear fragments and debris particles, distal from a bone-artificial component interface. The indentations can also provide a location for the accumulation of wear fragments and/or debris particles that is not directly adjacent to a contact region of the surface of the component, thereby minimizing further wear at the contact surface of the joint through grinding of accumulated wear fragments.

In some embodiments, the artificial joint components include at least one component configured to magnetically shield the component including at least one magnet. The shielding component can, for example, be configured to minimize the magnetic field's influence beyond the immediate joint region. A component configured to magnetically shield the component including at least one magnet can include, for example, an external shield component configured to mate with the external, or bone-facing, region of an acetabular cup component of an artificial hip joint. A component configured to magnetically shield the component including at least one magnet can include, for example, an external shield component configured to mate with the bone-facing region of a glenoid component of an artificial shoulder joint. A component configured to magnetically shield the component including at least one magnet can include, for example, an external shield component configured to mate with the bone-facing region of a tibial component of an artificial knee joint.

In some embodiments, the component including at least one magnet configured to create a magnetic field within the artificial joint includes wherein the magnetic field is configured to retain the debris including the magnetic particles in a location adjacent to a particle retaining structure within the artificial joint. For example, a particle retaining structure can be attached to one or more components of the artificial joint, and the magnetic field can be configured to influence the position of wear fragments and associated debris particles to that location within the joint. The particle retaining structure can subsequently retain the particles at that location independently of the magnetic field. Some embodiments include at least one particle retaining structure attached to the artificial joint prosthesis, the at least one particle retaining structure positioned in a location to retain the debris including the magnetic particles influenced by the magnetic field. Some embodiments include at least one particle retaining structure attached to the artificial joint prosthesis, the at least one particle retaining structure positioned in a location to retain the debris including the magnetic particles influenced by the magnetic field. Some embodiments include a particle retaining structure including a first edge region, the first edge region attached to at least one non-contact surface a first component of the artificial joint; and the particle retaining structure including a second edge region, the second edge region attached to at least one non-contact surface of a second component of the artificial joint.

The material used to fabricate a particle retaining structure will vary depending on the embodiment. Factors in the selection of materials for a particle retaining structure include: cost of the materials, size of the particle retaining structure, shape of the particle retaining structure, stability of the particle retaining structure under the estimated physiological pressure of synovial fluid and joint motion in a given embodiment, and compatibility of the particle retaining structure with other components of the prosthetic implant. In some embodiments, a particle retaining structure is configured to surround the joint, (e.g. as a membrane configured as a sheath or tube around the joint and affixed at both ends to the artificial joint). A particle retaining structure can include components designed to ease the use of the joint, such as ring structures configured to encourage folding of the membrane during joint movement. See U.S. Pat. No. 5,514,182 "Prosthetic Joint with Semipermeable Capsule with Reinforcing Ribs," to Shea, which is incorporated herein by reference. Materials used to fabricate a particle retaining structure will be part of the prosthetic joint, and therefore should be suitable for implantation into a body (e.g. low toxicity and non-inflammatory). Materials used to fabricate a particle retaining structure should be expected to be durable throughout the anticipated duration of use of the prosthetic joint, for example no less than 10 years of routine physiological use in vivo. Materials suitable for fabrication of a particle retaining structure include, for example, silicone, hydroxyl-ethyl-methacrylate and polyvinylpirrolidone.

Some embodiments include a particle retaining structure that includes a first end, the first end affixed to the artificial joint prosthesis; and a second end, the second end affixed to an additional artificial joint component. For example, a particle retaining structure can include one or more membrane structures, each of which include a first end affixed to the artificial joint prosthesis, such as the acetabular liner of a hip joint, and a second end affixed to an additional artificial joint component, such as the region adjacent to the prosthesis-bone interface on the femoral component of the prosthesis. Some embodiments include a particle retaining structure that is affixed to a surface of the artificial joint prosthesis. For example, a particle retaining structure can be configured to reversibly mate with a surface of one or more components of a artificial joint. Some embodiments include a particle retaining structure that is affixed to a plurality of surfaces of the artificial joint prosthesis. Some embodiments include a particle retaining structure that is affixed to a plurality of components of the artificial joint prosthesis.

Some embodiments include at least one particle retaining structure including a plurality of apertures. For example, the plurality of apertures can be configured to be of a size and shape to physically entrap the expected wear fragments and other particles in the joint fluid. For example, a particle retaining structure can include a plurality of apertures having a diameter less than approximately 0.05 millimeters (mm). See, for example, U.S. Pat. No. 5,378,228 "Method and Apparatus for Joint Fluid Decompression and Filtration with Particulate Debris Collection," to Schmalzried and Jasty, which is incorporated herein by reference. Some embodiments include at least one particle retaining structure including a structure configured to retain non-physiological particles present in the synovial fluid. For example, the structure configured to retain non-physiological particles present in the synovial fluid can include apertures of the correct size and shape to retain the expected non-physiological particles, such as wear fragments, in the synovial fluid. For example, the structure configured to retain non-physiological particles present in the synovial fluid can include a coating expected to bind to non-physiological particles, such as a coating including one or more antibodies, or a coating containing one or more chemically reactive species. Some embodiments include at least one particle retaining structure including a structure configured to retain particles containing artificial materials, including polymers. For example, the structure configured to retain non-physiological particles present in the synovial fluid can include a magnetic coating configured to bind ferromagnetic particles present in the fluid, such as magnetic particles in wear fragments.

Some embodiments include at least one fluid deflecting structure attached to a non-contact surface of the artificial joint. One or more fluid deflecting structures can, for example, be configured to operate synergistically with the magnetic field to influence the movement of debris particles including wear fragments to a desired location within the joint. Fluid deflecting structures can be configured, for example, as a flange or cuff-like structure attached to a non-contact surface of the artificial joint. Fluid deflecting structures can be configured, for example, as a plurality of ciliated projections. The optional fluid deflecting structures can be configured to divert synovial fluid flow away from the prosthesis-bone interface during physiological activity, and therefore to deflect wear fragments and debris in the synovial fluid. The optional fluid deflecting structures can be configured to divert synovial fluid and debris particles within the fluid away from the prosthesis-bone interface and towards a desired location, such as in accord with the magnetic field. The synovial fluid deflecting structures of the artificial joint prosthesis components described herein can also be configured to decrease the transient synovial fluid pressure at the prosthesis-bone interface during physiological activities. The reduction of synovial fluid flow as well as transient pressure at the bone-prosthesis interface will lead to a reduction of debris particles entering the prosthesis-bone interface during physiological movement. This will decrease the risk of osteolysis related to wear debris particles at the prosthesis-bone interface, thereby reducing the risk of prosthesis failure and the need for revision surgery with its associated costs and morbidity. In some embodiments, the prosthesis structures can include additional chemical inhibitors of osteolysis (see, e.g. Linden, ibid, and Mediero et al., "Adenosine $A_{2A}$ Receptor Activation Prevents Wear Particle-Induced Osteolysis," *Science Translational Medicine* 4(135ra65) (2012), which are each incorporated herein by reference).

The artificial joint prosthesis components described herein can include synovial fluid deflecting structures configured to deflect synovial fluid flow and associated particles away from the bone-prosthesis interface in combination with the magnetic fields as well as to mitigate the transient increase in synovial fluid pressure at the bone-prosthesis interface during physiological movement. In some embodiments, there are synovial fluid deflecting structures positioned on one component of an artificial joint prosthesis. In some embodiments, there are synovial fluid deflecting structures positioned on two or more components of an artificial joint prosthesis, with the synovial fluid deflecting structures configured to direct the location of debris particles in combination with the magnetic field during relative motion of the two or more components of an artificial joint prosthesis during in vivo use. In some embodiments, there are synovial fluid deflecting structures configured to induce angular momentum in the synovial fluid during physiological movement. The induced angular momentum of the synovial fluid results in deflection of the synovial fluid flow and associated wear particles away from the bone-prosthesis interface, and reduced transient pressure at the bone-prosthesis interface during physiological movement during in vivo use. In some embodiments, there are synovial fluid deflecting structures positioned on one or more of the joint components and configured to convert the force from the joint motion on the synovial fluid during physiological movement into a resulting synovial fluid flow in an inclined or orthogonal direction relative to the original synovial fluid flow. The converted inclined or orthogonal direction of the synovial fluid results in deflection of the synovial fluid flow and associated particulates away from the bone-prosthesis interface, and reduced transient pressure at the bone-prosthesis interface during physiological movement during in vivo use. The specific positioning, size, shape and configuration of the synovial fluid deflecting structures on the artificial joint prosthesis components will vary depending on the embodiment, including the specific type of artificial joint prosthesis, its size, the size of the associated joint in vivo, the strength and position of the magnetic field, and expected physiological forces on the associated synovial fluid when the artificial joint prosthesis is used in vivo.

The material used to fabricate a synovial fluid deflection structure will vary depending on the embodiment. Factors in the selection of materials for a fluid deflection structure include: cost of the materials, size of the fluid deflection structure, shape of the fluid deflection structure, flexibility of the fluid deflection structure under the estimated physiological pressure of synovial fluid in a given embodiment, and compatibility of the fluid deflection structure with other components of the prosthetic implant. Materials used to fabricate a fluid deflection structure will be part of the prosthetic joint, and therefore should be suitable for implantation into a body (e.g. low toxicity and non-inflammatory). Materials used to fabricate a fluid deflection structure should be expected to be durable throughout the anticipated duration of use of the prosthetic joint, for example no less than 10 years of routine physiological use in vivo. Materials suitable for fabrication of a synovial fluid deflection structure include, for example, polypropylene and silicone.

The artificial joints described herein can be used in conjunction with an external magnetic field. For example, the artificial joints described herein can be used with an external magnetic field to enhance or promote the movement of wear fragments including magnetic particles to a particular location within the joint. For example, an external magnetic field can be applied periodically with the external magnetic field configured to provide greater magnetic field strength to the existing field of the joint. The external field can operate additively or synergistically, for example, with the internal field of the joint. The artificial joints described herein can also be used in conjunction with an external magnetic field to determine the present, approximate number, concentration, and size of wear fragments including magnetic particles, for example. See U.S. Pat. No. 5,558,091, "Magnetic Determination of Position and Orientation," to Acker et al., which is incorporated herein by reference.

In some embodiments, the artificial joints described herein can be used in combination with an external alternating current (AC) magnetic field to create thermal energy (heat) in the magnetic particles in the joint. By heating the wear fragments, any cellular components that can be associated with the wear fragments can be lysed or dispersed. Removal of cellular components that can be associated with the wear fragments can reduce the immune response to the wear fragments, and release the wear fragments for repositioning within the joint in accord with the influence of the magnetic fields. The external magnetic field can be directed to the synovial fluid region of the joint selectively, and thereby configured to create heated particles only in the synovial region and not within the solid structural portions of the artificial joint.

For a more complete understanding of the embodiments, reference now is made to the following descriptions taken in connection with the accompanying drawings. The use of the same symbols in different drawings typically indicates similar or identical items, unless context indicates otherwise.

With reference now to FIG. 1, shown is an example of an artificial hip joint prosthesis depicted in vivo in cross-section that serves as a context for introducing one or more artificial joint prostheses including fluid deflecting structures as described herein. The artificial hip joint prosthesis depicted in FIG. 1 is depicted in cross-section in vivo in a resting, or not significantly physiologically flexed, position. The cross-section view depicted in FIG. 1 is a substantially planar view of a vertical cross-section through the hip joint. The embodiment illustrated in FIG. 1 includes a hip joint prosthesis including: a bone-facing surface of an artificial hip joint prosthesis, the bone-facing surface configured to face a bone-prosthesis interface in vivo; a first component of the artificial hip joint prosthesis including a contact surface of the artificial hip joint prosthesis, the first component fabricated from at least one polymer and a plurality of magnetic particles; and a second component of the artificial hip joint prosthesis including at least one magnet configured to create a magnetic field within the artificial hip joint, the at least one magnet positioned to form a magnetic field directed to influence a location of debris including the magnetic particles in the joint to a position distinct from the bone-prosthesis interface in vivo.

FIG. 1 illustrates a hip joint prosthesis 100 in vivo, with prosthetic components including an acetabular liner 140 which includes an exterior surface configured to reversibly mate with an interior surface of an acetabular cup or shell 170. The acetabular shell 170 includes a bone-facing surface 110, which forms a bone-prosthesis interface with the pelvis 160 in vivo, such as in the view shown in FIG. 1. The acetabular liner 140 shown also includes a bone-facing surface 120, which forms a bone-prosthesis interface in vivo. The acetabular liner 140 includes a contact surface 145, which corresponds with the majority of the interior surface of the concave acetabular liner 140. The contact surface 145 of the acetabular liner 140 comes into contact with the femoral ball 182 of the artificial joint during physiological use. For purposes of illustration in FIG. 1 the acetabular liner 140 and the femoral ball 182 are shown with a gap between them. The femoral ball 182 is attached to a femoral stem 187. The femoral stem 187 of the artificial hip joint 100 is implanted into a femur 165 for physiological use of the artificial hip joint. The femoral stem 187 includes a bone-facing surface 130 which forms a bone-prosthesis interface in vivo. The artificial hip joint 100 includes a particle retaining structure 190. In the illustrated embodiment, the particle retaining structure 190 is configured as a sheath or tubular structure around the synovial fluid region of the joint. The particle retaining structure 190 is attached at a first end to an edge of the acetabular liner 140. The particle retaining structure 190 is attached at a second end to the edge of the femoral stem 187 in a location adjacent to the bone-facing region 130 of the femoral stem 187.

FIG. 1 also illustrates that the acetabular shell 170 includes at least one magnet that forms a magnetic field 150 at the outer edge of the shell or cup structure. The magnetic field 150 is positioned to direct any magnetic particles that may be present in the synovial fluid to a location 155 distal to the bone-prosthesis interfaces. FIG. 1 shows that a particle retaining structure 190 is adjacent to the location 155 of the magnetic field 150 where magnetic particles will be attracted. The particle retaining structure 190 can retain some of the particles after the magnetic field 150 influences their position to that location 155 in the magnetic field 150.

Figure 2:
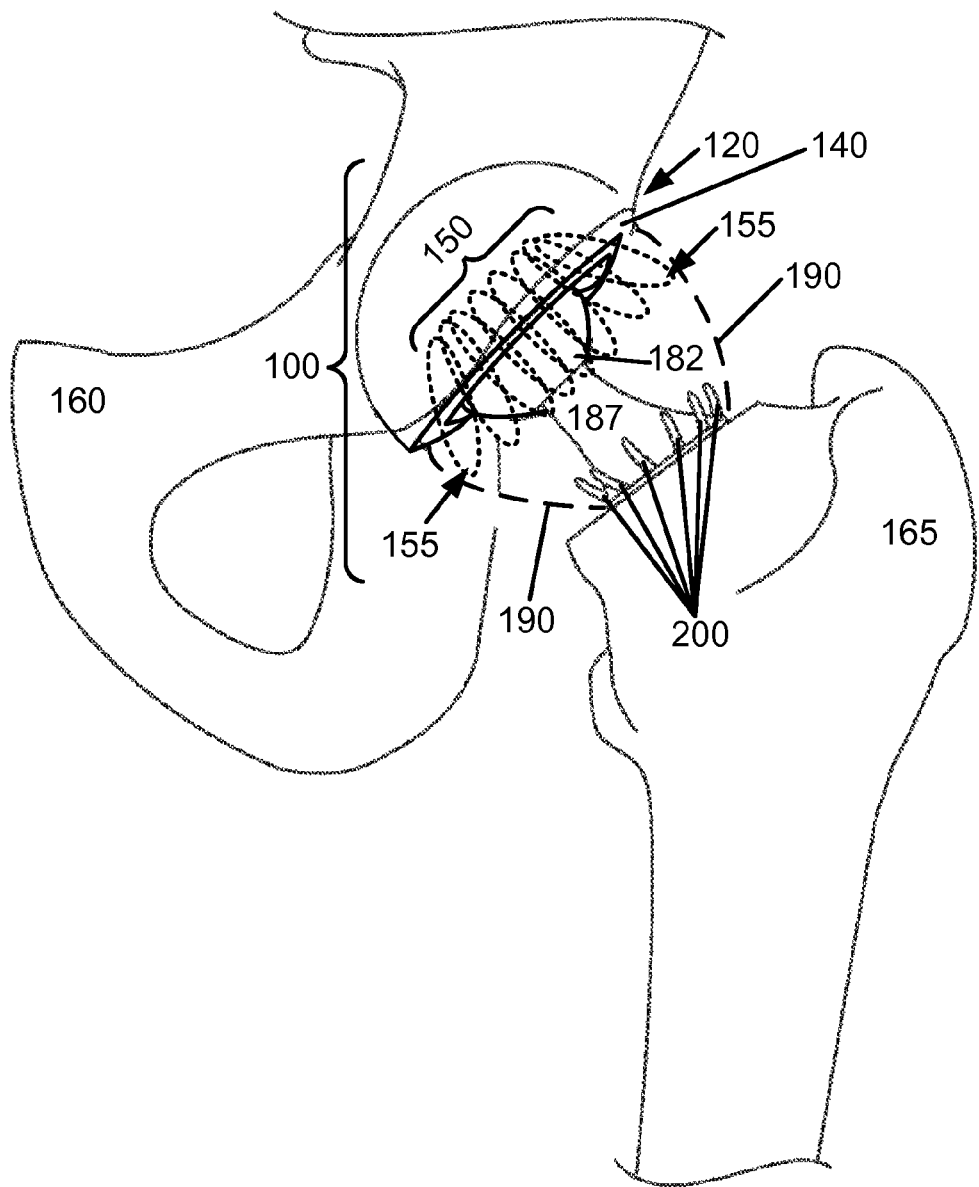
FIG. 2 shows an artificial hip joint as in FIG. 1, in an external view.

FIG. 2 illustrates an embodiment of an artificial hip joint 100 in vivo similar to that illustrated in FIG. 1. The view shown in FIG. 2 is an external view. For purposes of illustration, the rough size and shape of the acetabular liner 140 is drawn as an arc, although in actuality it would not be visible through the pelvis 160. FIG. 2 shows the edge of the acetabular liner 140 is visible adjacent to the bone-facing surface 120 of the acetabular liner 140. The acetabular shell includes a plurality of magnets, which form a composite magnetic field 150. The magnetic field 150 is oriented so that it creates a series of locations 155 where magnetic particles present in the synovial fluid would be attracted around the femoral ball 182 adjacent to the femoral stem 187. The locations 155 form a ring around the femoral ball 182. The locations 155 would encourage magnetic particles present in the synovial fluid to positions adjacent to the particle retaining structure 190, which surrounds the synovial fluid region of the joint 100.

The embodiment shown in FIG. 2 also includes a plurality of particle deflecting structures 200 attached to the femoral stem 187 on a surface of the femoral stem 187 adjacent to the femoral stem 187-bone interface. The particle deflecting structures 200 are configured as a series of ciliated, curvilinear structures. The particle deflecting structures 200 are positioned to operate in conjunction with the magnetic field 150 to encourage debris or particulates present in the synovial fluid toward the particle retaining structure 190 and away from the bone-prosthesis interfaces.

Figure 3:
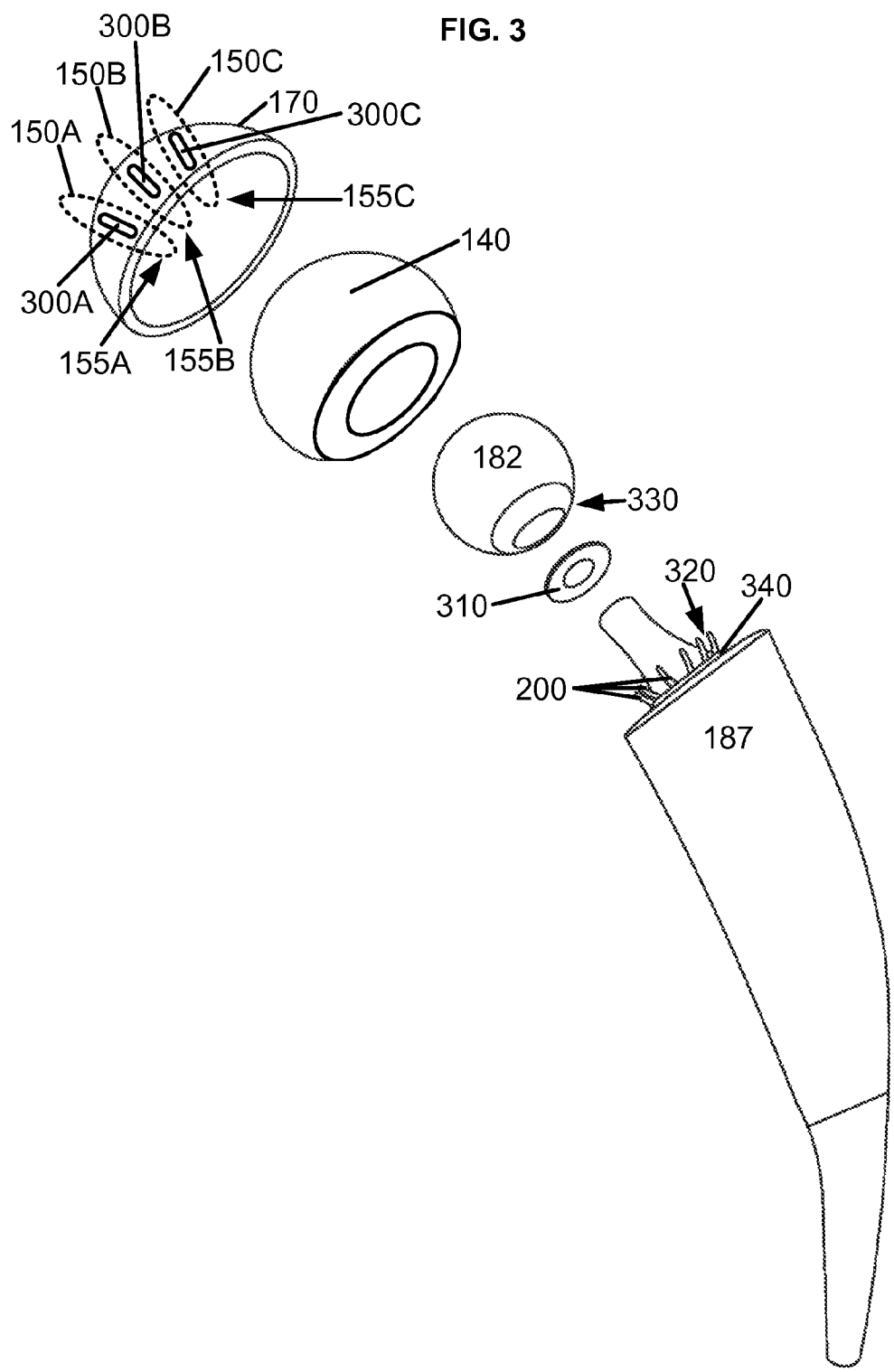
FIG. 3 depicts components of an artificial hip joint.

FIG. 3 illustrates aspects of an artificial hip joint ex vivo. The artificial hip joint shown includes a femoral stem 187 configured to be implanted in a femur bone. The femoral stem 187 includes a non-contact surface 320. On the non-contact surface 320 of the femoral stem 187, a plurality of particle deflecting structures 200 are attached to a restraining band 340. The plurality of particle deflecting structures 200 are configured as a series of ciliated, curvilinear structures surrounding the non-contact surface 320 of the femoral stem 187. The band 340 is secured in position relative to the non-contact surface 320 of the femoral stem 187 by a groove or channel in the non-contact surface 320 of the femoral stem 187.

Also shown in FIG. 3 is a femoral ball 182. The femoral ball 182 includes a non-contact region 330 in a circular zone around the region where the femoral ball 182 attaches to the femoral stem 187. A particle retaining structure 310 is configured as a flat disk structure with a surface configured to mate with the non-contact surface 330 of the femoral ball 182. The femoral ball 182 is of a size and shape to reversibly fit within the acetabular liner 140 during physiological use of the artificial hip joint. During use, the interior region of the acetabular liner 140 would form a contact surface relative to the femoral ball 182. The acetabular liner 140 is fabricated from at least one polymer and a plurality of magnetic particles.

FIG. 3 illustrates a acetabular shell 170 including an interior surface configured to mate with the outer surface of the acetabular liner 140. The acetabular shell 170 includes a plurality of magnets 300A, 300B, 300C. For the purposes of clearer illustration, only 3 magnets are shown on one side of the acetabular liner 140, however it is expected that a plurality of magnets 300 would encircle the acetabular shell 170 in most embodiments. Each of the magnets 300A, 300B, 300C generates a magnetic field 150A, 150B, 150C. Each of the magnetic fields 150A, 150B, 150C creates a location 155A, 155B, 155C which would influence a location of debris including the magnetic particles in the joint to a position distinct from the bone-prosthesis interface in vivo. The magnetic fields 150A, 150B, 150C can be positioned and oriented to form at least one cooperating array. See, for example: U.S. Patent Application Publication No. 2003/0195633, "Magnetic Array Implant and Prosthesis Insert" to Hyde; and U.S. Pat. No. 7,811,328, "System, Device, and Methods for Replacing the Intervertebral Disk with a Magnetic or Electromagnetic Prosthesis, to Molz et al., which are each incorporated herein by reference.

Figure 4:
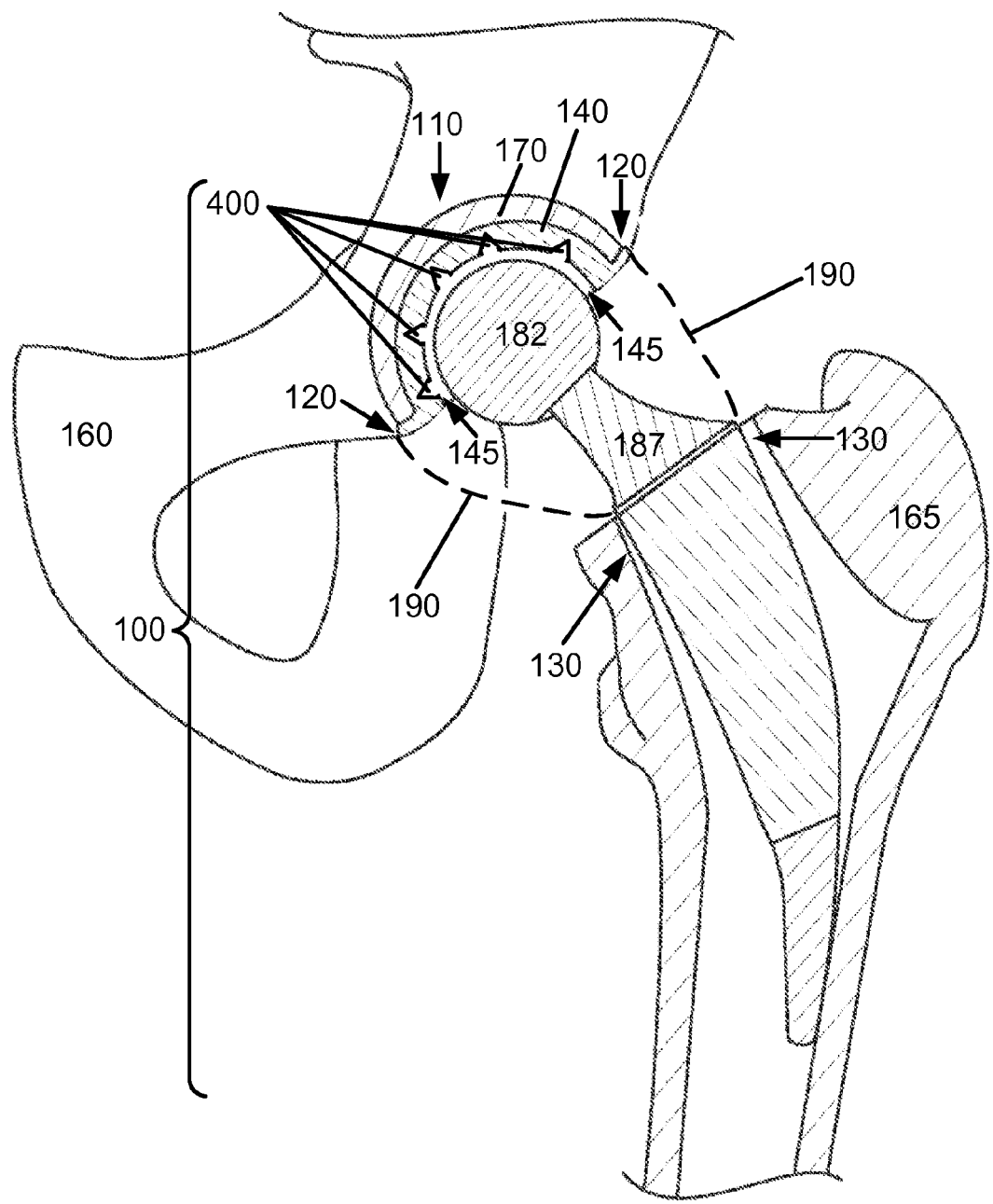
FIG. 4 illustrates a artificial hip joint in cross-section.

FIG. 4 illustrates aspects of an artificial hip joint 100 shown in cross-section in vivo. The artificial hip joint 100 includes an acetabular liner 140 which includes an exterior surface configured to reversibly mate with an interior surface of an acetabular shell 170. The acetabular shell 170 includes a bone-facing surface 110, which forms a bone-prosthesis interface with the pelvis 160 in vivo, such shown in FIG. 4. The acetabular liner 140 shown also includes a bone-facing surface 120, which forms a bone-prosthesis interface in vivo. The acetabular liner 140 includes a contact surface 145, which includes the majority of the interior surface of the concave acetabular liner 140. The contact surface 145 of the acetabular liner 140 comes into contact with the femoral ball 182 of the artificial joint during physiological use. The acetabular liner 140 and the femoral ball 182 are shown in FIG. 4 with a space between them. The femoral ball 182 is attached to a femoral stem 187. The femoral stem 187 of the artificial hip joint 100 is implanted into a femur 165. The femoral stem 187 includes a bone-facing surface 130 which forms a bone-prosthesis interface in vivo. The artificial hip joint 100 includes a particle retaining structure 190. In the illustrated embodiment, the particle retaining structure 190 is configured as a sheath or tubular structure surrounding the synovial fluid region of the joint. The particle retaining structure 190 is attached at a first end to an edge of the acetabular liner 140. The particle retaining structure 190 is attached at a second end to the edge of the femoral stem 187 in a location adjacent to the bone-facing region 130 of the femoral stem 187.

FIG. 4 also illustrates that the contact surface 145 of the acetabular liner 140 includes a series of indentations 400. The indentations 400 are shown as groove structures. Although not illustrated for purposes of clarity, the acetabular shell 170 in an embodiment such as that shown in FIG. 4 can include a series of magnets configured to form at least one magnetic field that attracts magnetic particles to the surface of the acetabular liner 140. The magnetic field can attract magnetic particles, such as fragments of the acetabular liner 140, into the indentations 400 in the contact surface 145. The magnetic field can be formed by a cooperative array from a series of magnets.

In some embodiments, an artificial hip joint includes: a bone-facing surface of an artificial hip joint prosthesis, the bone-facing surface configured to face a bone-prosthesis interface in vivo; a first component of the artificial hip joint prosthesis including a contact surface of the artificial hip joint prosthesis, the first component fabricated from at least one polymer and a plurality of magnetic particles; and a second component of the artificial hip joint prosthesis including at least one magnet configured to create a magnetic field within the artificial hip joint, the at least one magnet positioned to form a magnetic field directed to influence a location of debris including the magnetic particles in the joint to a position distinct from the bone-prosthesis interface in vivo. The bone-facing surface of the artificial hip joint prosthesis can be formed by one or more of: a region of a shell of a acetabular component; a region of a liner of a acetabular component; or a region of a stem of a femoral component.

In some embodiments, the first component of an artificial hip joint is an acetabular component of a hip joint prosthesis or a head of a femoral component of a hip joint prosthesis. In some embodiments, the first component of an artificial hip joint is fabricated from a polymer including the plurality of magnetic particles embedded in a polymer matrix. In some embodiments, the first component of an artificial hip joint is fabricated from polyethylene including the plurality of magnetic particles embedded in a polymer matrix. In some embodiments, the first component of an artificial hip joint is fabricated from at least one magnetic polymer nanocomposite material. In some embodiments, the first component of an artificial hip joint is fabricated from a polymer including a plurality of magnetic nanoparticles at an average density no less than 10 magnetic nanoparticles per square micron ($\mu m^2$) of the polymer. In some embodiments, the first component of an artificial hip joint is fabricated from a polymer including a plurality of magnetic nanoparticles at an average density no less than 100 magnetic nanoparticles per square micron ($\mu m^2$) of the polymer.

The first component can include one or more indentations at the contact surface. The indentations can be, for example, cuts, channels, or gaps at the surface. The indentations are not sufficiently deep to significantly alter the structural integrity of the component or the contact surface. The first component can include one or more grooves in the contact surface. See, e.g. FIG. 4.

In some embodiments, the second component of an artificial hip joint is an acetabular liner component or a stem of a femoral component. In some embodiments, the second component is fabricated with an interior region proximal to the contact surface of the hip joint, the interior including at least one magnet and an exterior region distal to the hip joint, the exterior region including magnetic shielding. Some embodiments include a plurality of magnets, which can be positioned and oriented to form a cooperative array. For example, some embodiments of an artificial hip joint include a plurality of magnets integral to the acetabular shell, the magnets positioned around the circumference of the shell and oriented to create a cooperative array forming a magnetic field around the shell. In some embodiments, the second component of an artificial hip joint includes at least one permanent magnet. In some embodiments, the second component of an artificial hip joint includes at least one electromagnet. In some embodiments, the second component includes wherein the magnetic field is configured to retain the debris including the magnetic particles in a location adjacent to a surface of the second structural component. In some embodiments, the second component includes wherein the magnetic field is configured to retain the debris including the magnetic particles in a location adjacent to a particle retaining structure within the artificial hip joint.

Some embodiments of an artificial hip joint include at least one particle retaining structure. Some embodiments include at least one particle retaining structure attached to the artificial hip joint prosthesis, the at least one particle retaining structure positioned in a location to retain the debris including the magnetic particles influenced by the magnetic field. Some embodiments include at least one particle retaining structure attached to at least one non-contact surface of the artificial hip joint. Some embodiments include a particle retaining structure including a first edge region, the first edge region attached to at least one non-contact surface a first component of the artificial hip joint; and the particle retaining structure including a second edge region, the second edge region attached to at least one non-contact surface of a second component of the artificial hip joint. See, e.g. FIGS. 1, 2 and 4.

Figure 5:
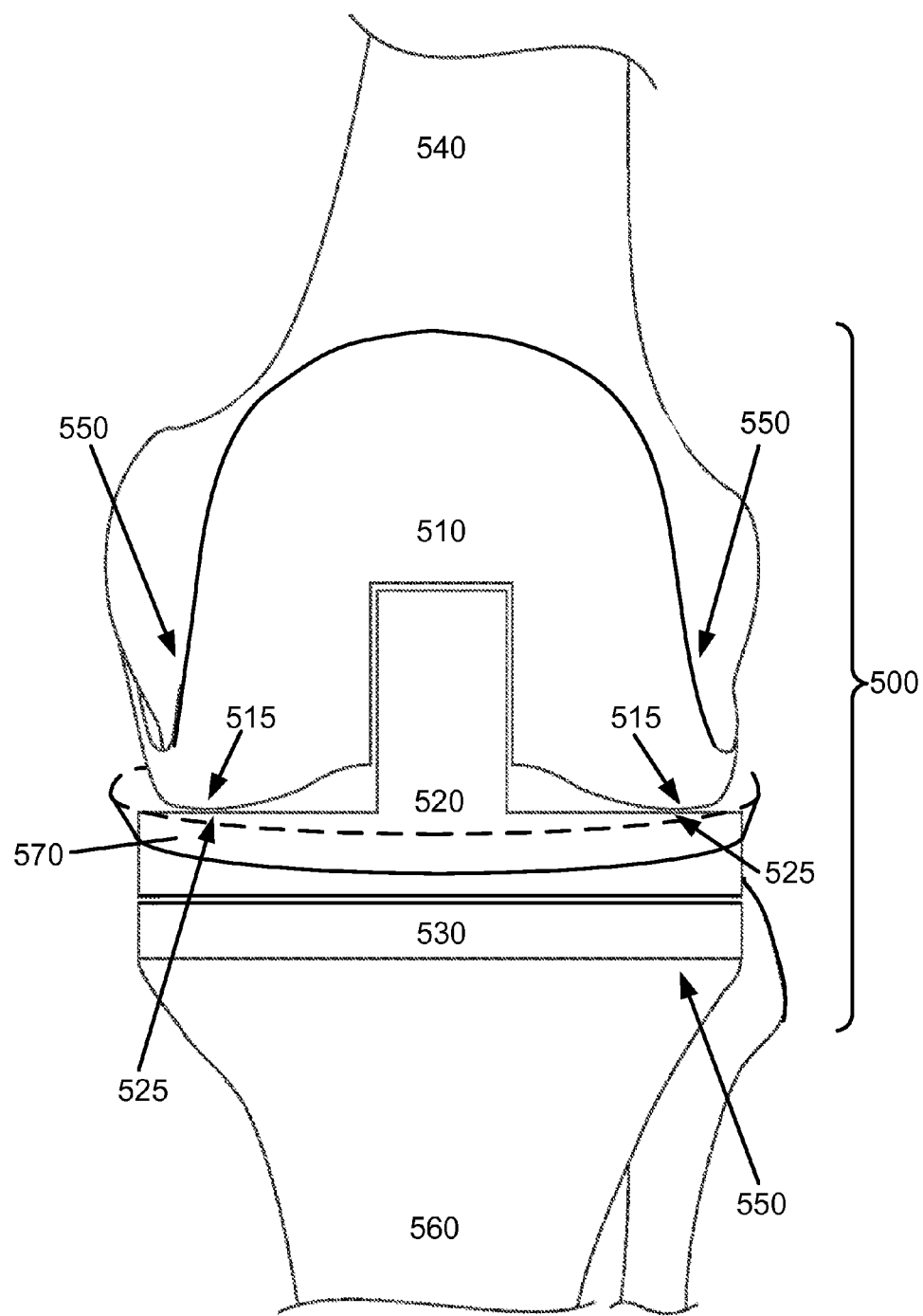
FIG. 5 depicts an external, frontal view of an artificial knee joint.

FIG. 5 illustrates an artificial knee joint 500 in a frontal, external view. A femoral component 510 of the artificial knee joint 500 is attached to the femur 540. The femoral component 510 has a bone-facing surface 550, which forms a bone-prosthesis interface in situ, as shown in FIG. 5. The femoral component 510 includes at least two contact surfaces 515, which come into contact with the tibial contact component 520 during physiological use of the artificial knee joint 500. The tibial contact component 520 includes contact surfaces 525 which come into contact with the corresponding contact surfaces 515 of the femoral component 510 during physiological use of the artificial knee joint 500. In the embodiment illustrated in FIG. 5, the tibial contact component 520 has an attached particle retaining structure 570 attached to a non-contact region of the tibial contact component 520. In the embodiment illustrated, the particle retaining structure 570 is configured as a flange structure, with a cuff-like shape that encircles the outer, non-contact region of the tibial contact component 520. The artificial knee joint 500 includes a tibial support element 530 which attaches to the tibia 560 in situ. The tibial support element 530 includes a bone-facing surface 550, which forms a bone-prosthesis interface with the tibia 560.

The artificial knee joint 500 illustrated in FIG. 5 includes a bone-facing surface of an artificial knee joint prosthesis, the bone-facing surface configured to face a bone-prosthesis interface in vivo. Both the femoral component 510 and the tibial support element 530 include bone-facing surfaces 550. The embodiment illustrated also includes components including contact surfaces 515, 525. Either or both of the components including contact surfaces 515, 525 can be fabricated from at least one polymer and a plurality of magnetic particles, depending on the embodiment. For example, the femoral component 510 can be fabricated from a polymer including a plurality of magnetic particles with sufficient density to expect that wear fragments from the contact surface 515 would include magnetic particles embedded in the polymer. For example, the tibial contact component 520 can be fabricated from a polymer including a plurality of magnetic particles. In some embodiments, both the femoral component 510 and the tibial contact component 520 are fabricated from polymer material including a plurality of magnetic particles embedded in the material.

Although not shown in FIG. 5 in the interest of clarity, the artificial knee joint 500 includes at least one component including at least one magnet configured to create a magnetic field within the artificial knee joint, the at least one magnet positioned to form a magnetic field directed to influence a location of debris including the magnetic particles in the joint to a position distinct from the bone-prosthesis interface in vivo. For example, the tibial support element 530 can include a plurality of magnets arranged as an array, the array forming a composite magnetic field that directs any magnetic particles, including wear fragments from the contact surfaces 515, 525, to a position distinct from the bone-prosthesis interfaces.

Figure 6:
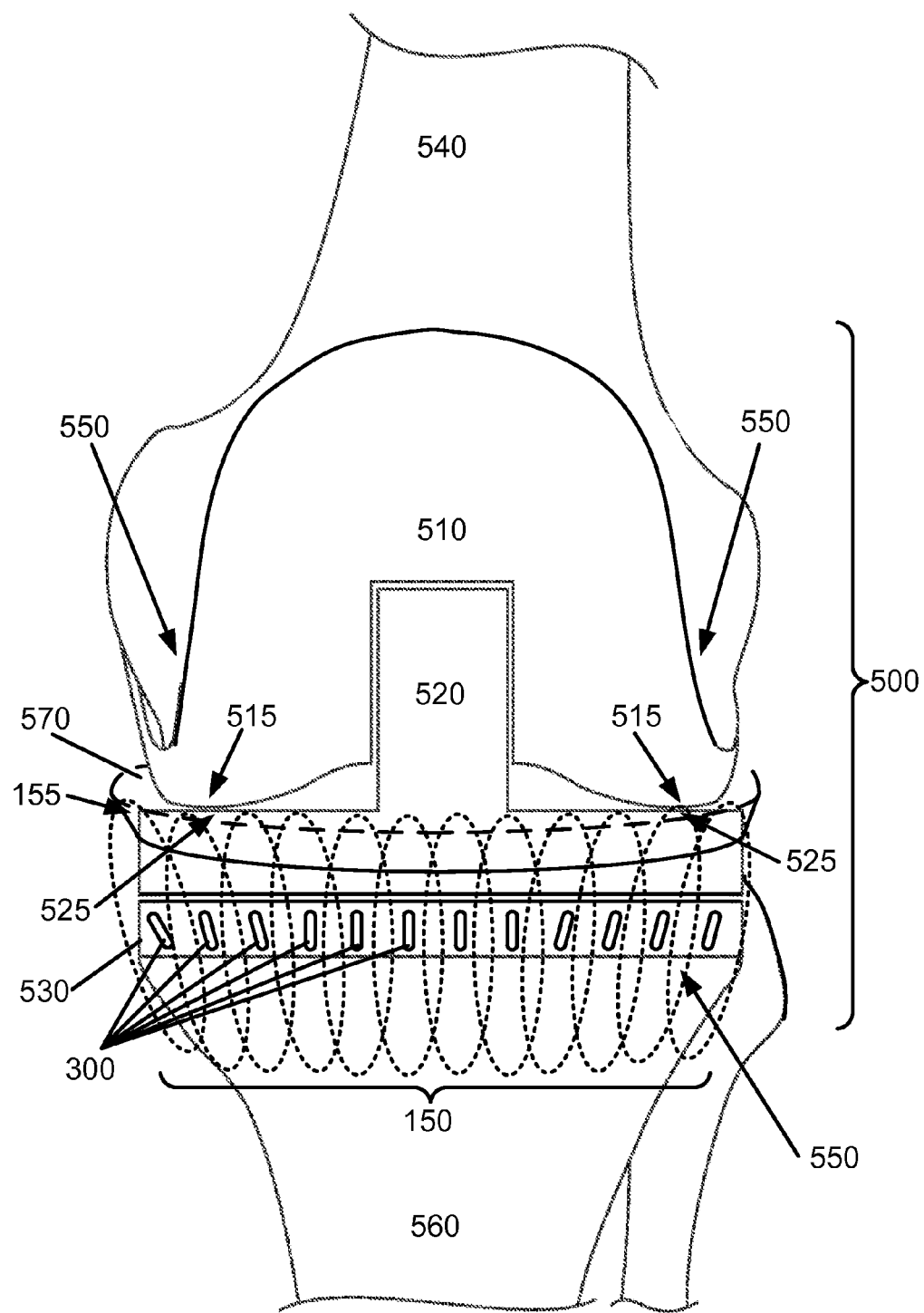
FIG. 6 shows further aspects of an artificial knee joint as illustrated in FIG. 5.

FIG. 6 illustrates an embodiment of an artificial knee joint 500 including a femoral component 510, a tibial contact component 520 and a tibial support component 530. The view shown is similar to that illustrated in FIG. 5, although FIG. 6 depicts the tibial support component 530 with a plurality of magnets 300 embedded in the structure. For the purposes of illustration, the plurality of magnets 300 and their corresponding magnetic fields are shown in FIG. 6, although it is to be expected that these would not ordinarily be visible. For purposes of illustration, not all of the magnets are explicitly marked 300. The plurality of magnets 300 form a composite magnetic field 150 that would be expected to attract wear fragments from the contact surfaces 515, 525 to a position 155 distal to the bone-prosthesis interfaces. The position 155 shown in FIG. 6 is the edge of the magnetic field 150, which forms a ring-like structure around the center region of the artificial knee joint 500. The position 155 of the magnetic field where magnetic particles, including wear fragments, would be attracted corresponds roughly with the distal edge of the particle retaining structure 570. The particle retaining structure 570 is configured to retain the magnetic particles in its structure or on its surface. The magnetic field 150 and the particle retaining structure 570 illustrated in FIG. 6 are configured to work synergistically in vivo, with the magnetic field 150 directing any wear fragments present in the synovial fluid to a position 155 adjacent to the particle retaining structure 570. The probability is, therefore, increased that during physiological use of the artificial knee joint 500 any wear fragments present in the synovial joint fluid will be sequestered by the particle retaining structure 570. The sequestering of wear fragments by the particle retaining structure 570 will decrease the possibility of wear fragments entering a bone-prosthesis interface region, and correspondingly decrease the possibility of osteolysis and associated prosthesis failure.

Figure 7:
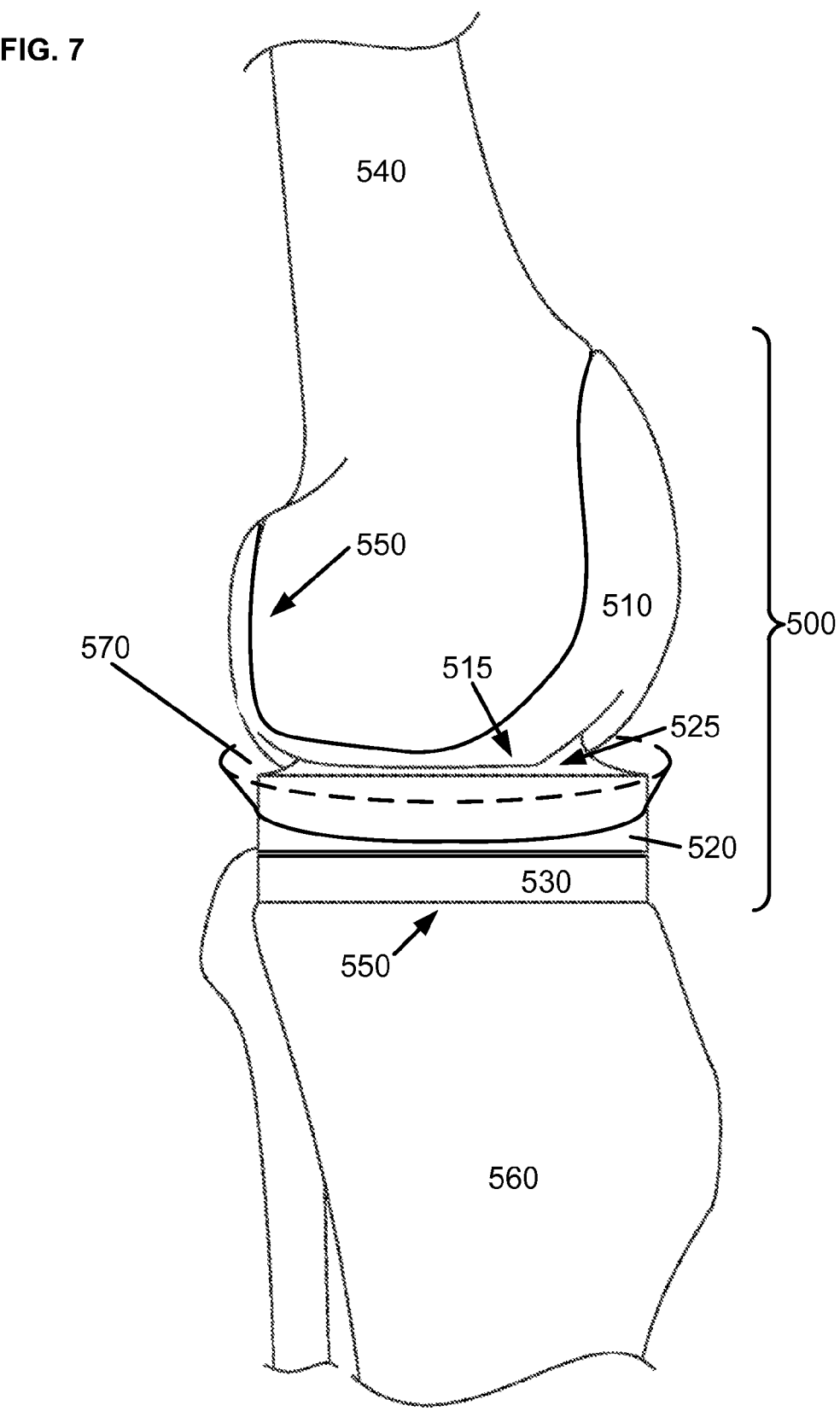
FIG. 7 illustrates a side view of an artificial knee joint.

FIG. 7 illustrates a side view of an artificial knee joint 500 such as that shown in FIG. 5. FIG. 7 shows that the artificial knee joint 500 includes a femoral component 510, which has a contact surface 515. The artificial knee joint 500 includes a tibial contact component 520, which includes a contact surface 525. The contact surfaces 515, 525 are expected to come into contact during physiological use of the joint, and also to include weight-bearing surfaces. The artificial knee joint 500 also includes a tibial support component 530 attached to a tibia 560. The femoral component 510 and the tibial support component 530 both include bone-facing surfaces 550, each of which are part of a bone-prosthesis interface in vivo. A particle retaining structure 570 is attached to the tibial contact component 520. The particle retaining structure 570 is configured as a flange or cuff-like structure encircling the exterior, non-contact region of the tibial contact component 520.

Figure 8:
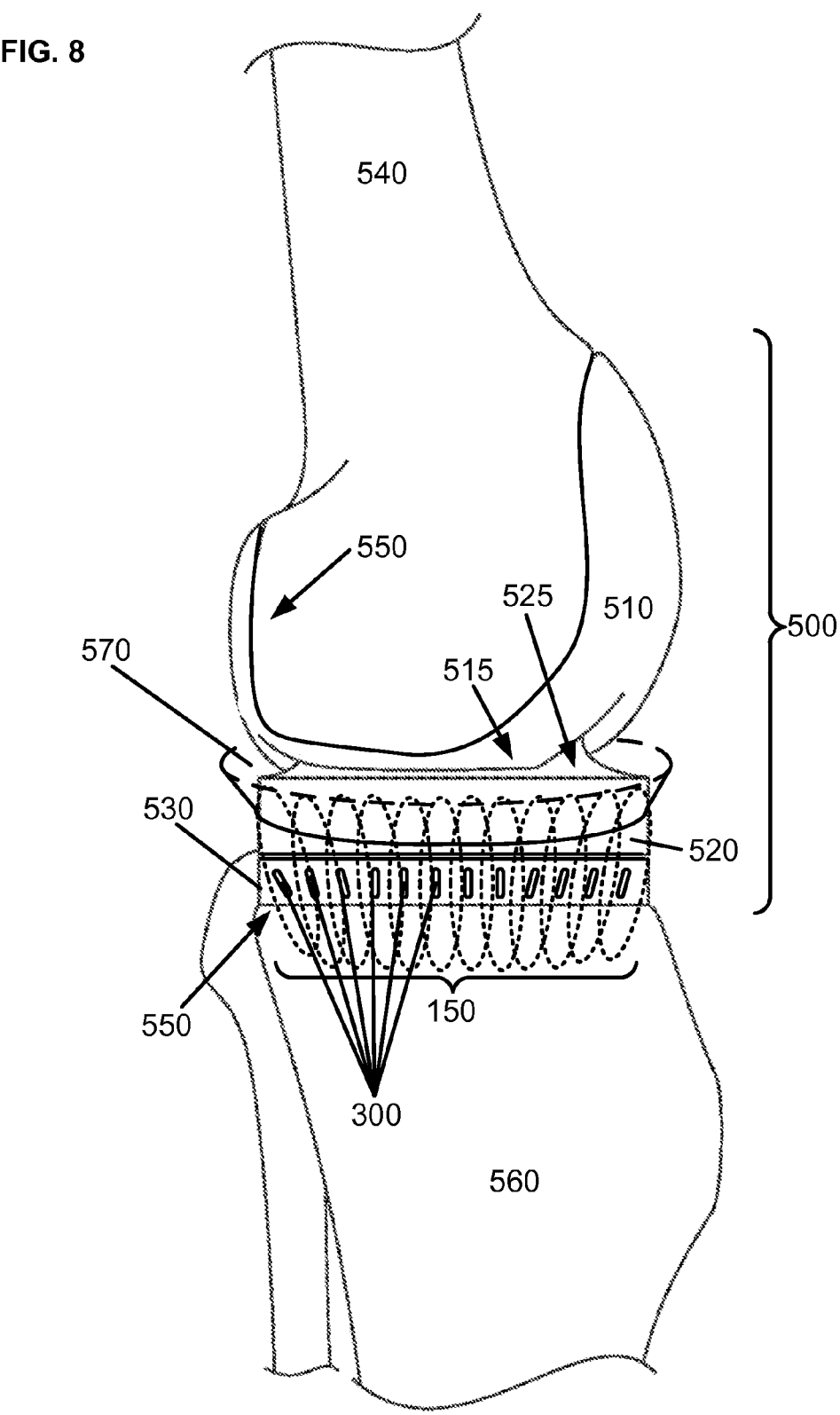
FIG. 8 shows further aspects of an artificial knee joint in a side view as shown in FIG. 7.

FIG. 8 illustrates a side view of an artificial knee joint 500, a similar view as shown in FIG. 7. FIG. 8 illustrates that the tibial support component 530 includes a plurality of magnets 300 embedded in the structure. For the purposes of illustration, the plurality of magnets 300 and their corresponding magnetic fields are shown in FIG. 8, although it is to be expected that these would not ordinarily be visible. For purposes of illustration, not all of the magnets are explicitly marked 300. The plurality of magnets 300 form a composite magnetic field 150 that would be expected to attract wear fragments from the contact surfaces 515, 525 to a position 155 distal to the bone-prosthesis interfaces. The position 155 is adjacent to the distal edge of the particle retaining structure 570. As described relative to FIG. 6, the magnetic field 150 and the particle retaining structure 570 shown in FIG. 8 are configured to work synergistically in vivo, with the magnetic field 150 directing wear fragments present in the synovial fluid to a position 155 adjacent to the particle retaining structure 570.

Figure 9:
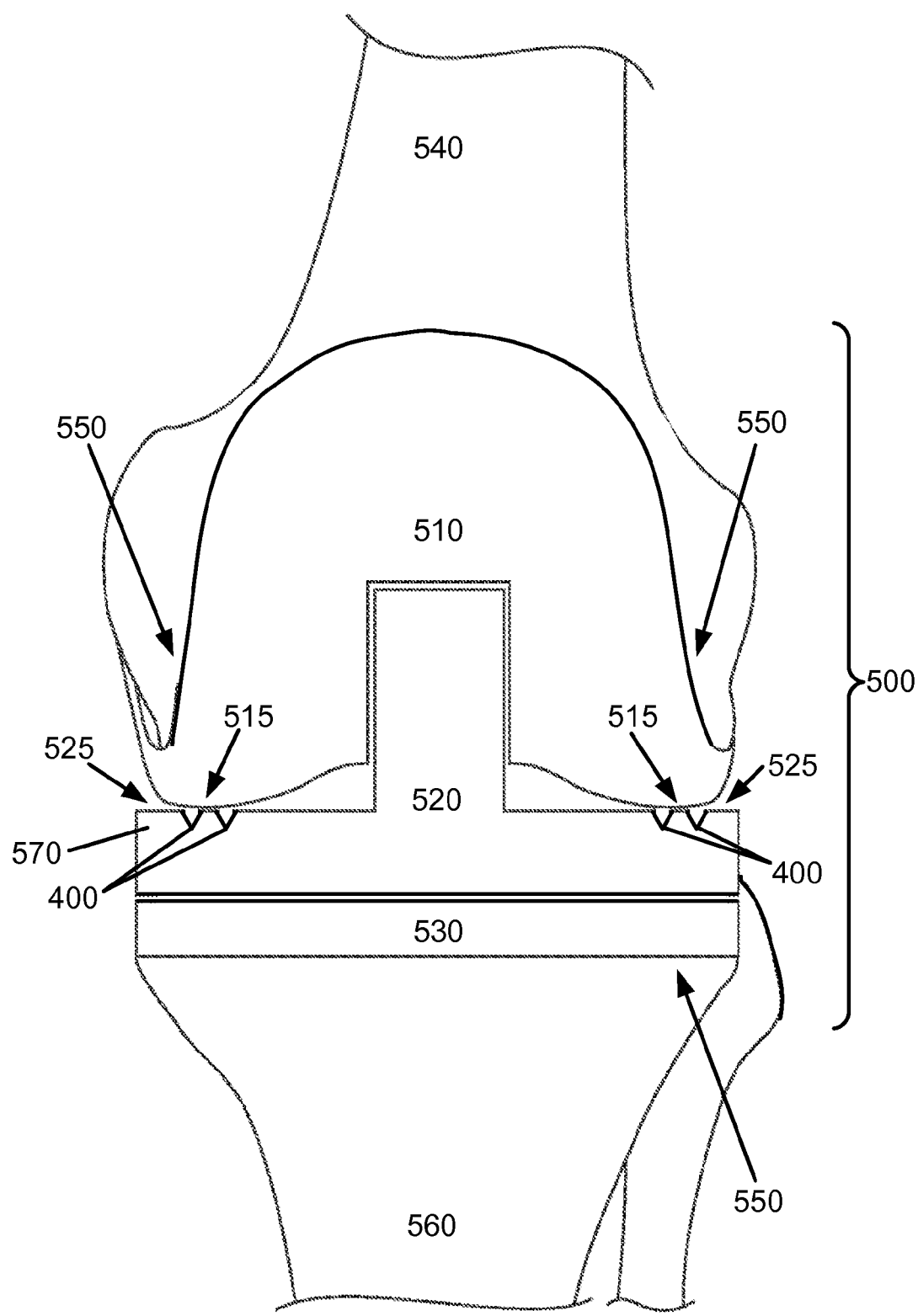
FIG. 9 depicts an external, frontal view of an artificial knee joint.

FIG. 9 illustrates aspects of an artificial knee joint 500 in vivo. The view shown is similar to that of FIG. 5, above. FIG. 9 illustrates an artificial knee joint 500 including a femoral component 510 which has a contact surface 515. The femoral component 510 is configured to reversibly mate with the tibial contact component 520, which also includes a contact surface 525. The femoral component 510 and the tibial contact component 520 are expected to have moving contact with friction at the contact surfaces 515, 525 of each of the components during physiological use of the joint. The femoral component 510 and the tibial contact component 520 are fabricated from at least one polymer and a plurality of magnetic particles with sufficient density so that wear fragments from either contact surface 515, 525 will include magnetic particles. The tibial contact component 520 is secured to the tibial support element 530, which is correspondingly attached to the tibia 560. As shown in FIG. 9, the contact surface 525 of the tibial contact component 520 includes indentations 400 at the surface. The indentations 400 are configured as channels or grooves in the contact surface 525. The indentations 400 are not large or deep enough to substantially impair the structural integrity of the tibial contact component 520. Although not illustrated in FIG. 9, the artificial joint 500 includes at least one magnet configured to create a magnetic field within the artificial knee joint, the at least one magnet positioned to form a magnetic field directed to influence a location of debris including the magnetic particles in the joint to a position distinct from the bone-prosthesis interface in vivo. The at least one magnet, and the corresponding magnetic field, are configured to attract wear fragments, including magnetic particles, from the contact surfaces 515, 525 in the indentations 400. The positioning of the wear fragments, including magnetic particles, into the indentations 400 is expected to minimize debris particles at the bone-prosthesis interface in vivo.

As described above relative to FIGS. 5-9, an artificial knee joint includes a bone-facing surface of an artificial knee joint prosthesis, the bone-facing surface configured to face a bone-prosthesis interface in vivo. The bone-facing surface can include, for example, a region of a femoral component, or a region of a tibial component. The artificial knee joint also includes a first component of the artificial knee joint prosthesis including a contact surface of the artificial knee joint prosthesis, the first component fabricated from at least one polymer and a plurality of magnetic particles. The first component can include, for example: a femoral component of a knee joint prosthesis; a tibial component of a knee joint prosthesis; or a patellar component of a knee joint prosthesis. Some embodiments include a plurality of components fabricated from at least one polymer and a plurality of magnetic particles. The artificial knee joint further includes a second component of the artificial knee joint prosthesis including at least one magnet configured to create a magnetic field within the artificial knee joint, the at least one magnet positioned to form a magnetic field directed to influence a location of debris including the magnetic particles in the joint to a position distinct from the bone-prosthesis interface in vivo. For example, in some embodiments, the second component is at least one of: a femoral liner of a knee joint prosthesis; a tibial liner of a knee joint prosthesis; or a patellar component of a knee joint prosthesis.

The first component of the artificial knee joint prosthesis is fabricated from at least one polymer and a plurality of magnetic particles. In some embodiments, the first component is fabricated from a polymer including the plurality of magnetic particles embedded in a polymer matrix. In some embodiments, the first component is fabricated from polyethylene including the plurality of magnetic particles embedded in a polymer matrix. In some embodiments, the first component is fabricated from at least one magnetic polymer nanocomposite material. In some embodiments, the first component is fabricated from a polymer including a plurality of magnetic nanoparticles at an average density no less than 10 magnetic nanoparticles per square micron ($\mu m^2$) of the polymer. In some embodiments, the first component is fabricated from a polymer including a plurality of magnetic nanoparticles at an average density no less than 100 magnetic nanoparticles per square micron ($\mu m^2$) of the polymer.

In some embodiments, the first component includes a contact surface with one or more indentations at the contact surface. The indentations can be formed, for example, as patterns, channels or regions of the contact surface. In some embodiments, the first component includes a contact surface with one or more grooves in the contact surface. The knee joint prosthesis can be configured so that wear fragments from the contact surface are attracted to the interior region of the indentations or grooves through magnetic attraction.

An artificial knee joint includes a second component including at least one magnet configured to create a magnetic field within the artificial knee joint, the at least one magnet positioned to form a magnetic field directed to influence a location of debris including the magnetic particles in the joint to a position distinct from the bone-prosthesis interface in vivo. In some embodiments, the second component is fabricated with an interior region proximal to the contact surface of the knee joint, the interior including at least one magnet and an exterior region distal to the knee joint, the exterior region including magnetic shielding. In some embodiments, the second component includes at least one permanent magnet. In some embodiments, the second component includes at least one electromagnet. In some embodiments, the second component including at least one magnet configured to create a magnetic field within the artificial knee joint includes wherein the magnetic field is configured to retain the debris including the magnetic particles in a location adjacent to a surface of the second structural component. In some embodiments, the second component including at least one magnet configured to create a magnetic field within the artificial knee joint includes wherein the magnetic field is configured to retain the debris including the magnetic particles in a location adjacent to a particle retaining structure within the artificial joint.

Some embodiments of an artificial knee prosthesis include at least one particle retaining structure attached to at least one non-contact surface of the artificial knee joint. Some embodiments of an artificial knee prosthesis include at least one particle retaining structure attached to the artificial knee joint prosthesis, the at least one particle retaining structure positioned in a location to retain the debris including the magnetic particles influenced by the magnetic field. Some embodiments include a particle retaining structure including a first edge region, the first edge region attached to at least one non-contact surface a first component of the artificial knee joint; and the particle retaining structure including a second edge region, the second edge region attached to at least one non-contact surface of a second component of the artificial knee joint. Some embodiments include at least one fluid deflecting structure attached to a non-contact surface of the artificial knee joint. For example, a fluid deflecting structure can be positioned as well as of a size and shape to deflect particles in the synovial fluid in the direction of a particle retaining structure. A fluid deflecting structure can be configured to operate in conjunction with a magnetic field in the joint.

Figure 10:
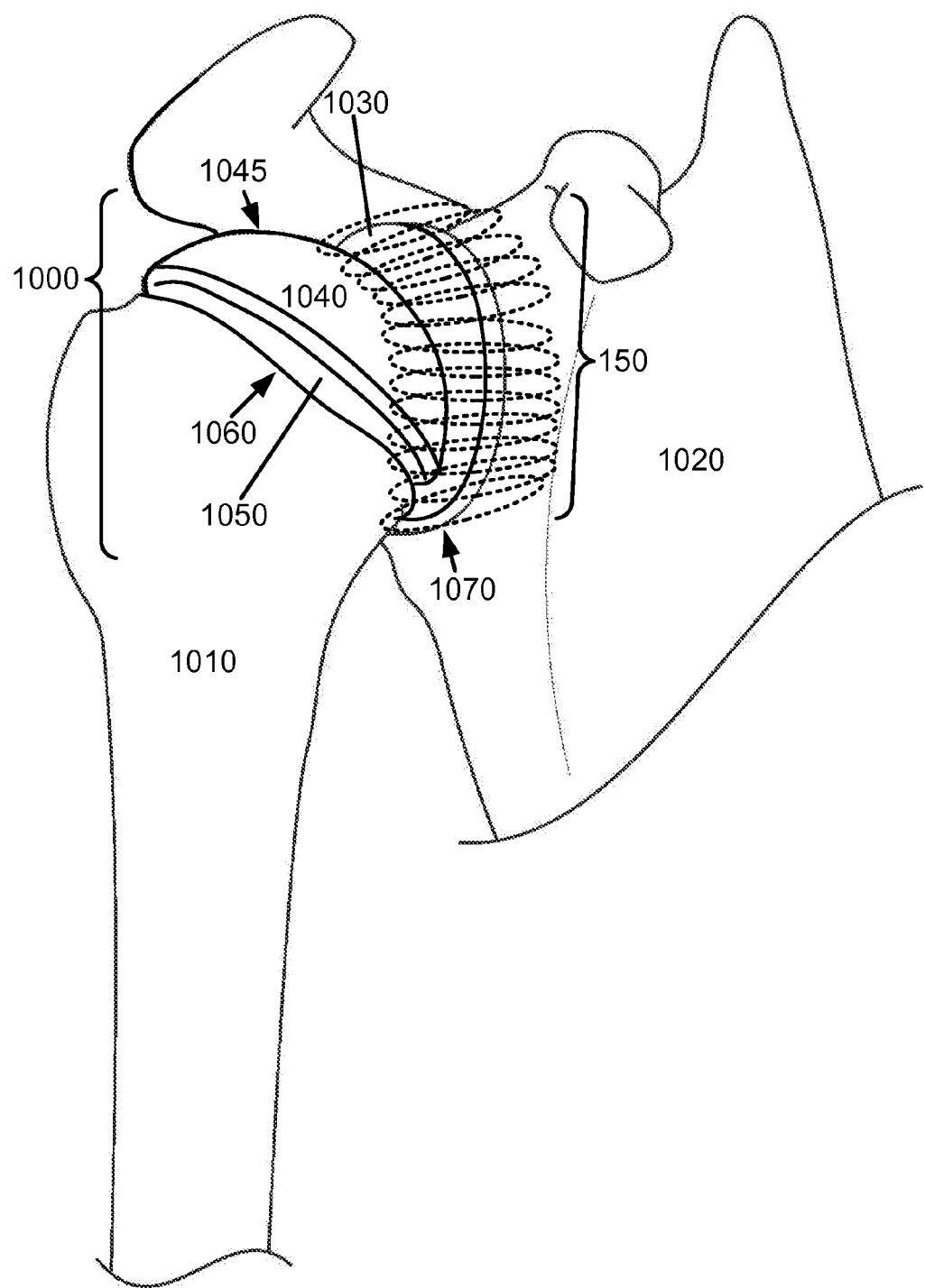
FIG. 10 illustrates an artificial shoulder joint.

FIG. 10 illustrates aspects of an artificial shoulder joint prosthesis. An artificial shoulder joint prosthesis includes: a bone-facing surface of an artificial shoulder joint prosthesis, the bone-facing surface configured to face a bone-prosthesis interface in vivo; a first component of the artificial shoulder joint prosthesis including a contact surface of the artificial shoulder joint prosthesis, the first structural component fabricated from at least one polymer and a plurality of magnetic particles; and a second component of the artificial shoulder joint prosthesis including at least one magnet configured to create a magnetic field within the artificial shoulder joint, the at least one magnet positioned to form a magnetic field directed to influence a location of debris including the magnetic particles in the joint to a position distinct from the bone-prosthesis interface in vivo. In some embodiments, the bone-facing surface includes one or more of: a region of a humeral stem of the shoulder joint prosthesis; a region of a humeral component of the shoulder joint prosthesis; or a region of a glenoid component to a scapula of the shoulder joint prosthesis. In some embodiments, the first component includes one or more of: a humeral component of the shoulder joint prosthesis, or a glenoid component to a scapula of the shoulder joint prosthesis.

FIG. 10 shows an artificial shoulder joint 1000 in vivo. The artificial shoulder joint 1000 includes a glenoid component 1030 with a bone-facing surface 1070. The bone-facing surface 1070 forms a bone-prosthesis interface with the scapula 1020. The artificial shoulder joint 1000 also includes a humeral component 1040. The humeral component 1040 includes a contact surface 1045, the contact surface 1045 configured to make contact with the glenoid component 1030 during physiological use of the joint 1000. The artificial shoulder joint 1000 includes a humeral support component 1050, which attaches to the humeral component 1040. The humeral support component 1050 includes a bone-facing surface 1060, which forms a bone-prosthesis interface with the humerus 1010 in vivo. Although not shown in the view illustrated in FIG. 10, the glenoid component 1030 includes a plurality of magnetics configured as an array. The magnets configured as an array create a magnetic field 150 around the glenoid component 1030. The magnetic field is directed to influence a location of debris including the magnetic particles in the joint to a position distinct from the bone-prosthesis interface in vivo.

An artificial shoulder joint prosthesis includes a first component of the artificial shoulder joint prosthesis including a contact surface of the artificial shoulder joint prosthesis, the first structural component fabricated from at least one polymer and a plurality of magnetic particles. In some embodiments, the first component is fabricated from a polymer including the plurality of magnetic particles embedded in a polymer matrix. In some embodiments, the first component is fabricated from polyethylene including the plurality of magnetic particles embedded in a polymer matrix. In some embodiments, the first component is fabricated from at least one magnetic polymer nanocomposite material. In some embodiments, the first component is fabricated from a polymer including a plurality of magnetic nanoparticles at an average density no less than 10 magnetic particles per square micron ($\mu m^2$) of the polymer. In some embodiments, the first component is fabricated from a polymer including a plurality of magnetic nanoparticles at an average density no less than 100 magnetic particles per square micron ($\mu m^2$) of the polymer.

In some embodiments, the first component includes one or more indentations at the contact surface. For example, the first component can include one or more channels or patterns in the contact surface. In some embodiments, the first component includes one or more grooves in the contact surface. The grooves or indentations in the contact surface are configured to maintain the structural integrity of the contact surface. In some embodiments, the magnetic field is configured to attract wear fragments including magnetic particles to a space within the grooves or indentations in the contact surface.

An artificial shoulder joint prosthesis includes a second component of the artificial shoulder joint prosthesis including at least one magnet configured to create a magnetic field within the artificial shoulder joint, the at least one magnet positioned to form a magnetic field directed to influence a location of debris including the magnetic particles in the joint to a position distinct from the bone-prosthesis interface in vivo. The second component can include, for example, a humeral component of the shoulder joint prosthesis, or a glenoid liner of the shoulder joint prosthesis. In some embodiments, the second component is fabricated with an interior region proximal to the contact surface of the shoulder joint, the interior including at least one magnet and an exterior region distal to the joint, the exterior region including magnetic shielding. In some embodiments, the second component includes at least one permanent magnet. In some embodiments, the second component includes at least one electromagnet. Some embodiments include wherein the second component including at least one magnet configured to create a magnetic field within the artificial shoulder joint includes wherein the magnetic field is configured to retain the debris including the magnetic particles in a location adjacent to a surface of the second structural component. Some embodiments include wherein the second component including at least one magnet configured to create a magnetic field within the artificial shoulder joint includes wherein the magnetic field is configured to retain the debris including the magnetic particles in a location adjacent to a particle retaining structure within the artificial shoulder joint.

Some embodiments of an artificial shoulder joint prosthesis include at least one particle retaining structure. For example, some embodiments include at least one particle retaining structure attached to at least one non-contact surface of the artificial shoulder joint. Some embodiments include at least one particle retaining structure attached to the artificial joint prosthesis, the at least one particle retaining structure positioned in a location to retain the debris including the magnetic particles influenced by the magnetic field. Some embodiments include a particle retaining structure including a first edge region, the first edge region attached to at least one non-contact surface of a first component of the artificial shoulder joint; and the particle retaining structure including a second edge region, the second edge region attached to at least one non-contact surface of a second component of the artificial shoulder joint. Some embodiments include at least one fluid deflecting structure attached to a non-contact surface of the artificial shoulder joint. The fluid deflecting structure and the particle retaining structure can be configured to work synergistically with the magnetic field to decrease the probability that wear fragments from the contact surface of the artificial joint will enter the bone-prosthesis interface in vivo.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components, devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components. In some instances, one or more components may be similarly referred to herein as "configured to," "configured by," "configurable to," "operable/operative to," "adapted/adaptable," "able to," "conformable/conformed to," etc.

This application may make reference to one or more trademarks, e.g., a word, letter, symbol, or device adopted by one manufacturer or merchant and used to identify and/or distinguish his or her product from those of others. Trademark names used herein are set forth in such language that makes clear their identity, that distinguishes them from common descriptive nouns, that have fixed and definite meanings, or, in many if not all cases, are accompanied by other specific identification using terms not covered by trademark. In addition, trademark names used herein have meanings that are well-known and defined in the literature, or do not refer to products or compounds for which knowledge of one or more trade secrets is required in order to divine their meaning. All trademarks referenced in this application are the property of their respective owners, and the appearance of one or more trademarks in this application does not diminish or otherwise adversely affect the validity of the one or more trademarks. All trademarks, registered or unregistered, that appear in this application are assumed to include a proper trademark symbol, e.g., the circle R or bracketed capitalization (e.g., [trademark name]), even when such trademark symbol does not explicitly appear next to the trademark. To the extent a trademark is used in a descriptive manner to refer to a product or process, that trademark should be interpreted to represent the corresponding product or process as of the date of the filing of this patent application.

EXAMPLES

Example 1

An Artificial Hip Joint Including Fluid Deflector Structures Configured to Divert and Diffuse Synovial Fluid Flow A hip joint prosthesis is fabricated with fluid deflector structures on select non-contact surfaces of the device. The fluid deflector structures are designed to divert joint fluids away from interfaces between the artificial device and the patient's bone, and to reduce the velocity of fluid flow in the artificial joint, thereby reducing the likelihood of aseptic loosening of the prosthetic implant. The fluid deflector structures are also configured to minimally impede joint function and mobility in vivo. The hip joint prosthesis includes a femoral component which includes a head (or ball), a neck attached to the head, and a stem which is configured to be implanted in the medullary canal of the femur. See, e.g. FIG. 1. The hip joint prosthesis also includes an acetabular component which forms a socket. The socket of the acetabular component includes an outer and inner cup, with the outer cup configured to be attached to pelvic bone and the inner cup configured to bear the head of the femoral component. See, e.g. FIGS. 1 and 2.

The neck and stem of the femoral component are made from titanium (see e.g., U.S. Pat. No. 6,761,741, "Prosthetic Joint," to Iesaka and US Patent Application No. 2003/0229398 "Prosthetic Joint," to Iesaka, which are each incorporated herein by reference). The femoral component of the artificial joint is fabricated by processes of investment casting and milling. For example, a solid model comprised of a thermally labile material (e.g., wax) is made by injection molding and then a ceramic shell is created by coating the solid wax model. The ceramic shell is recovered after melting the solid model and used as a mold to cast the femoral component of the prosthesis. See e.g., U.S. Pat. No. 5,665,118, "Bone Prostheses with Direct Cast Macrotextured Surface Regions and Method for Manufacturing the Same," to LaSalle et al., which is incorporated herein by reference.

At the base of the femoral component neck and the top of the femoral component stem, a row of fluid deflector structures (see e.g. FIGS. 2 and 3) are attached. The fluid deflector structures are positioned and shaped in a manner predicted to deflect synovial fluids away from the interface between the femur and the implanted stem, and to diffuse the fluid pressure at the interface, thus reducing the possibility of periprosthetic bone resorption (see e.g., Fahlgren et al., "Fluid Pressure and Flow as a Cause of Bone Resorption," *Acta Orthopaedica* 81: 508-516, 2010 which is incorporated herein by reference). The fluid deflector structures are fabricated from polyethylene and include a band linking an edge of each of a series of the fluid deflector structures at a set orientation relative to the circumference of the band. The base of the femoral component neck and the top of the femoral component stem are machined to include small surface grooves positioned to stabilize the fluid deflection structures. Each groove corresponds to the size and shape of the band linking a series of the fluid deflector structures (see, e.g. FIG. 3).

Fluid deflector structures are created from polyethylene in suitable shapes and sizes to line the border between the titanium stem and the femur and configured to deflect synovial fluid away from the stem-bone interface in vivo. Compression molding is used to form the polymeric fluid deflector structures directly onto the metallic stem at the site of the groove. See e.g., U.S. Pat. No. 5,879,404, "Acetabular Cups and Methods of their Manufacture," issued to Bateman et al. and U.S. Pat. No. 6,368,354, "Acetabular Bearing Assembly for Total Hip Joints," issued to Burstein, which are each incorporated herein by reference. Fluid deflector structures approximately 1 cm long and 0.5 cm in width are cast to protrude around the circumference of the femoral stem in a configuration predicted to divert synovial fluid away from the bone-stem interface and to reduce the transient synovial fluid pressure during physiological use of the joint. The fluid deflector structures are flexible, but firm enough to remain extended above the surface of the prosthesis and positioned to guide synovial fluid flow away from the stem-bone interface in vivo. See FIGS. 2 and 4. For example, a model hip joint subjected to axial and torsional forces displays high and low pressure in the proximal posterior and proximal anterior areas respectively of the femoral stem (see e.g., Bartlett et al., "In Vitro Influence of Stem Surface Finish and Mantle Conformity on Pressure Generation in Cemented Hip Arthroplasty," *Acta Orthopaedica* 80: 139-143, 2009 which is incorporated herein by reference). Fluid pressure differentials drive high estimated synovial fluid flow rates (e.g., 20 mm/s) and promote osteolysis that is observed in vivo in animal models of bone resorption (see e.g., Fahlgren et al., ibid., which is incorporated herein by reference). Fluid deflector structures are constructed to occlude the interface between the prosthesis stem and femoral bone and to reduce the transient pressure and divert the flow of joint fluid during physiological movement.

The acetabular component of the artificial joint is constructed using a process of investment casting that employs titanium in the outer cup and titanium and polyethylene in the inner cup (see e.g., U.S. Pat. No. 5,665,118 ibid. which is incorporated herein by reference). During the casing process, fluid deflector structures are constructed from polyethylene and integrally formed at the margin of the outer cup. These fluid deflection structures are fabricated of a size and shape expected to divert synovial fluid away from the interface between the pelvic bone and the outer cup during in vivo use. See, e.g. FIGS. 2 and 3. Manufacture of acetabular cups with titanium and polyethylene components is described (see e.g., U.S. Pat. No. 5,879,404, ibid. which is incorporated herein by reference).

If desired, a hip joint prosthesis can be surgically implanted that includes both a femoral component with fluid deflection structures attached and an acetabular cup with fluid deflection structures attached, as described above. A medical caregiver can also select a hip joint prosthesis that has fluid deflection structures attached to either the femoral component or the acetabular component. In this situation, the corresponding components without fluid deflection structures can be obtained for implantation in conjunction with the component with fluid deflection structures attached. For example, a femoral component with a titanium stem and a cobalt chromium alloy head is available from Stryker Orthopaedics, Mahwah, N.J. A acetabular component with a titanium shell and polyethylene bearings is available from Stryker Orthopaedics, Mahwah, N.J.

Example 2

An Artificial Knee Joint Including Fluid Deflector Structures and an Encapsulation/Filtration Membrane Configured to Retain Particulates A knee joint prosthesis is fabricated with fluid deflector structures on select non-contact surfaces of the device. The fluid deflector structures are of a size, shape and position expected to divert joint fluids away from the interfaces of the device and the patient's bone, thereby reducing the likelihood of aseptic loosening of the prosthetic implant. The knee joint prosthesis is fabricated including a filter membrane configured to capture debris particles arising in the joint that can be present in the joint fluid. The fluid deflector structures are configured to divert fluid flow through the filter, promoting removal of debris particles from the joint fluid. Polyethylene and metal debris particles in joint fluid, for example, are generally associated with osteolysis and loosening of artificial knee implants (see e.g., Collier et al., "Osteolysis After Total Knee Arthroplasty: Influence of Tibial Baseplate Surface Finish and Sterilization of Polyethylene Insert, Findings at Five to Ten Years Postoperatively," *J. Bone Joint Surg.* 87-A: 2702-2708, 2005 which is incorporated herein by reference).

The knee joint prosthesis comprises a femoral component and a tibial part including a tibial spacer, and a tibial tray component. The tibial spacer is fabricated from polyethylene. See e.g., U.S. Patent Application No. 2005/0055101 to Silheos, "Endoprosthesis of the Knee and/or Other Joints," which is incorporated herein by reference. For example, total knee replacement prostheses are commonly available including polyethylene components. See, e.g., Xie, "A Systematic Review on Performance of the Vanguard® Complete Knee System," Form No. BOI0500.0, REV083111, dated Jun. 30, 2011 and available from Biomet Inc., Warsaw, Ind., which is incorporated herein by reference. Other components are metallic, preferably fabricated from titanium.

Fluid deflector structures are created from polyethylene and attached to the knee prosthesis at non-contact surfaces of the prosthesis components. The fluid deflector structures are of a size and shape expected to deflect synovial fluid away from the prosthesis-bone interface. Compression molding methods are used to form the polymeric fluid deflector structures directly onto the metallic femoral component and tibial tray component (see e.g., U.S. Pat. No. 5,879,404, ibid. and U.S. Pat. No. 6,368,354, ibid, which are each incorporated by reference herein). Fluid deflector structures approximately 1 cm long and 0.5 cm in width are molded to protrude over the boundary of the femoral component and around the circumference of the tibial tray component.

At the margin of the femoral component adjacent to the prosthesis-bone interface a row of fluid deflector structures fabricated from polyethylene. The fluid deflector structures are configured to deflect synovial fluids away from the interface between the femur and the implanted femoral component, and to reduce the velocity of fluid flow in the joint, thus reducing periprosthetic bone resorption (see e.g., Fahlgren et al., ibid., which is incorporated herein by reference). A row of polyethylene fluid deflector structures is also attached to one or more of the tibial components and configured to divert and impede fluid flows away from the interface between the tibial component and bone.

The tibial tray component of the artificial joint is constructed using a process of investment casting (see e.g., U.S. Pat. No. 5,665,118 ibid., which is incorporated by reference herein) that employs titanium alloys. Fluid deflector structures constructed from polyethylene are formed on the margin of the tibial tray component to prevent synovial fluid from entering the interface between the tibial tray baseplate and the tibia. See Xie, ibid, which is incorporated by reference herein. Manufacture of prostheses with titanium and polyethylene components is as described (see e.g., U.S. Pat. No. 5,879,404, ibid, which is incorporated by reference herein).

The fluid deflector structures are flexible but firm enough to remain extended above the surface of the prosthesis and positioned to guide synovial fluid flow from transient regions of high fluid pressure to transient regions of low fluid pressure. For example, a model joint subjected to physiological axial and torsional forces displays relatively high and low pressure in the proximal posterior and proximal anterior areas respectively of a femoral stem (see e.g., Bartlett et al., 2009, ibid., which is incorporated by reference herein). Fluid pressure differentials result in high estimated fluid flow rates (e.g., 20 mm/s) which are associated with osteolysis and bone resorption (see e.g., Fahlgren et al., ibid., which is incorporated by reference herein). Fluid deflector structures are configured and attached so as to occlude the interface of the femoral component and bone where they divert and diffuse the flow of joint fluid. Fluid deflector structures are also of a size, shape and position to direct joint fluid flow toward a filter in the artificial joint. The combination of joint fluid flow diversion away from the bone-implant interface and toward a filter have synergetic effects to reduce the possible occurrence of osteolysis and implant loosening.

To remove debris particles in the joint, a membrane filter is fabricated to surround the artificial knee joint and trap particles present in the synovial joint fluid. Particles can, for example, arise from wear on the polyethylene or metal components of the joint. Particles can, for example, arise from debris remaining after the implantation surgery. Particulate debris arising from the articulating surfaces or elsewhere in the artificial joint are trapped by a membrane surrounding the joint components. The membrane surrounding the joint components is configured to trap debris particles while allowing joint fluid to pass through. A membrane filter comprised of silicone, hydroxyl-ethyl-methacrylate and polyvinylpirrolidone is fabricated to filter and trap particulates which may arise in the artificial joint (see U.S. Patent Application No. 2005/0055101, ibid., which is incorporated by reference herein). A membrane filter is constructed as a tube which attaches at one end to the bone adjacent to the tibial tray-tibia bone interface, while the distal end of the tube attaches to the femoral bone adjacent to the femoral component interface. Membrane filters are composed of laminates of polytetrafluoroethylene (PTFE) of different fibril lengths to trap particles less than 0.2 microns in diameter while allowing fluids to pass. See e.g.: U.S. Pat. No. 6,132,470, "Apparatus and Method for Protecting Prosthetic Joint Assembly from Wear," to Berman; U.S. Pat. No. 5,879,406 "Artificial Joint Bioprosthesis for Mitigation of Wear," to Lilley; U.S. Pat. No. 6,432, 141 "Joint Prosthesis Assembly and Method for Installing Same," to Stocks; US Patent Application No. 2003/0130740 "Joint Prosthesis Assembly and Method for Installing Same," to Stocks; U.S. Pat. No. 7,144,427 "Apparatus and Method for Advancing Synovial Fluid in a Prosthetic Joint," to Southworth; US Patent Application No. 2004/0111162 "Apparatus and Method for Advancing Synovial Fluid in a Prosthetic Joint," to Southworth; US Patent Application No. 2005/0055101 "Endoprosthesis of the Knee and/or other Joints," to Sifneos; and U.S. Pat. No. 5,571,195 "Prosthesis for an Artificial Joint Having Wear Particle Collection Capability," to Johnson, which are each incorporated herein by reference. Methods to attach a membrane filter to the bone adjacent to an artificial joint are described (see e.g.: U.S. Patent Application No. 2005/0055101, ibid.; U.S. Pat. No. 4,731,088, "Enclosure Member for Prosthetic Joint" to Collier; and U.S. Pat. No. 6,132,470, ibid., which are each incorporated by reference herein). The membrane filter can, in some embodiments, include one or more stay rings to minimize the possibility of mechanical entrapment of the membrane filter. See U.S. Pat. No. 5,514,182 "Prosthetic Joint with Semipermeable Capsule with Reinforcing Ribs," to Shea, which is incorporated herein by reference.

Example 3

An Artificial Hip Joint Including Actuated Fluid Deflector Structures Configured to Divert Synovial Fluid and Associated Debris Particles Away from Prosthesis-bone Interface An artificial hip joint prosthesis is fabricated with actuated fluid deflector structures attached to select non-contact surfaces of the device. The fluid deflector structures are configured to divert joint fluid and associated debris particles away from interfaces between the artificial joint and the patient's bones and to reduce the transient fluid pressure at the interfaces during physiological use of the joint. The fluid deflector structures are attached to mechanisms that move the fluid deflection structures and thereby alter fluid flow in the joint. The altered fluid flow is configured to reduce the likelihood of osteolysis and aseptic loosening of the prosthetic implant.

The hip joint prosthesis includes a femoral component which includes a head (or ball), a neck and a stem which is implanted in the medullary canal of the femur. There is also an acetabular component that includes an outer and inner cup with the outer cup attached to pelvic bone and the inner cup forming a socket bearing the head of the femoral component. The neck and stem of the femoral component are fabricated from titanium (see e.g., U.S. Pat. No. 6,761,741, ibid., which is incorporated herein by reference). Actuated fluid deflector structures are attached to non-contact surfaces on the edge regions of the femoral component and the acetabular component. The fluid deflector structures are configured to deflect synovial fluids and debris particles away from the interfaces between the prosthesis components and bone, and to mitigate the pressure of fluid flow on the prosthesis-bone interfaces, thus reducing the likelihood of periprosthetic bone resorption and artificial joint loosening (see e.g., Fahlgren et al., et al., ibid., which is incorporated herein by reference).

The artificial joint is fabricated using processes of investment casting and milling. For example, a solid model comprised of a thermally labile material (e.g., wax) is made by injection molding and then a ceramic shell is created by coating the solid wax model. The ceramic shell is recovered after melting the solid model and used as a mold to cast the components of the prosthesis. See e.g., U.S. Pat. No. 5,665, ibid., which is incorporated herein by reference. A groove is milled around the circumference of the femoral component at the base of the neck to stabilize attached actuated fluid deflector structures. A groove is also milled around the circumference of the acetabular component in the outer cup to stabilize attached actuated fluid deflector structures.

Actuated fluid deflector structures are constructed from polydimethylsiloxane (PDMS, available from Dow Corning Corp., Midland, Mich.) containing permanently magnetic nanoparticles. Carbon coated iron particles approximately 70 nm in diameter (available from M K Impex Corp., Missisauga, ON, Canada) are dispersed in PDMS and spin cast to obtain fluid deflector structures approximately 1 cm long and 3 mm wide. See e.g., Willem van Engen, Master's Thesis: "Artificial cilia for microfluidics exploring the use of a horizontally microstructured ferromagnetic PDMS composite," Eindhoven University of Technology, 2008, Eindhoven, Netherlands, which is incorporated herein by reference. The fluid deflector structures are magnetized by repeated movement of a permanent magnet with a magnetic field of about 500 mTesla along the long axis of the fluid deflector structures. The fluid deflector structures are attached to a polymeric band by adhesion and the bands, containing approximately 2 fluid deflector structures per centimeter, are inserted in the grooves of the femoral and acetabular components.

Magnetic fluid deflector structures approximately 1 cm long and 3 mm in width are positioned around the circumference of the femoral stem and the acetabular cup in positions predicted to divert synovial fluid away from the bone-stem interface and to mitigate transient high pressure in the joint fluid due to physiological movement of the joint. The fluid deflector structures are flexible but firm enough to remain extended above the surface of the prosthesis and positioned to guide synovial fluid flow. For example, a model hip joint subjected to axial and torsional forces displays high and low pressure in the proximal posterior and proximal anterior areas respectively of the femoral stem (see e.g., Bartlett et al., 2009, ibid., which is incorporated herein by reference). Fluid pressure differentials and high estimated fluid flow rates (e.g., 20 mm/s) promote osteolysis and bone resorption (see e.g., Fahlgren et al., ibid., which is incorporated herein by reference). Magnetic fluid deflector structures are configured to mitigate fluid flow and pressure at the interface of the prosthesis and bone in vivo. The magnetic fluid deflector structures can be fabricated from polyethylene including magnetic nanoparticles. See: Chatterjee et al., "Synthesis of Polyethylene Magnetic Nanoparticles," European Cells and Materials 3(2): 98-101 (2002); Wang et al., "Novel Magnetic Polyethylene Nanocomposites Produced by Supported Nanometer Magentic Ziegler-Natta Catalyst," *Polymer International* 49: 184-188 (2000); Millan et al., "Magnetic Polymer Nanocomposites," chapter 17 in Polymer Nanocomposites, Mai and Yu, eds. CRC Press, 2006; and Killeya, "First Plastic Magnets Created," *New Scientist* (30 Aug. 2004), which are each incorporated herein by reference.

A permanent magnet is constructed within the femoral component and configured to actuate the magnetic deflectors. A permanent magnet with a magnetic field of approximately 500 mTesla is placed in the stem region of the femoral component to form a magnetic field configured to interact with the magnetic fluid deflector structures on the femoral and acetabular components as the hip joint moves. The permanent magnet within the femoral component has a size, shape and position expected to create a magnetic field that is roughly perpendicular to the fluid deflector structures. For example, a magnetic field of approximately 50 mTesla applied perpendicular to the magnetic deflectors causes a deflection of approximately 0.5 millimeter in an artificial cilia (see van Engen, ibid., which is incorporated herein by reference).

Alternatively, an electromagnet can be used to actuate the fluid deflector structures. See US Patent Application No. 2008/0306324 "Magnetic Joint Implant," to Bonutti and Beyers, which is incorporated herein by reference. Reversing the direction of electrical current in the electromagnet switches the magnetic field direction by 180 degrees and reverses the direction of movement of the magnetic fluid deflector structures. An electromagnet can be used to create a magnetic field of approximately 500 mTesla, increasing the deflection of the magnetic fluid deflector structures by 10 fold relative to a 50 mTesla magnetic field. Moreover, rapid switching of the direction of the magnetic field will result in "beating" of the magnetic fluid deflector structures to actively divert synovial fluid flow away from prosthesis-bone interfaces. The electromagnet can be empowered by a battery or piezoelectric elements in the artificial hip prosthesis. Piezoelectric devices suitable to capture and store energy from the movement of an artificial joint are known (see e.g., Keawboonchuay et al., "Maximum Power Generation in a Piezoelectric Pulse Generator," IEEE Transactions On Plasma Science, 31: 123-128, 2003, which is incorporated herein by reference).

Example 4

An Artificial Hip Joint Including Actuated Fluid Deflector Structures Configured to Capture Debris Particles A hip joint prosthesis is fabricated with actuated fluid deflector structures on select non-contact surfaces of the device. The actuated fluid deflector structures are configured to divert joint fluid and debris particles away from the interface regions between the implanted artificial joint and the patient's bones. Also the actuated fluid deflector structures include distal edge regions with adhesive tips. The adhesive regions of the actuated fluid deflector structures are configured to capture and sequester debris particles in the joint fluid. Debris particles within the joint fluid are associated with an increased likelihood of osteolysis and aseptic loosening of the prosthetic implant.

The hip joint prosthesis includes a femoral component which includes a head (or ball), a neck, and a stem which is configured to be implanted in the medullary canal of the femur. The hip joint prosthesis also includes an acetabular component that includes an outer and inner cup, with the outer cup configured to be attached to pelvic bone and the inner cup forming a socket that bears the head of the femoral component in vivo. The neck and stem of the femoral component are made from titanium (see e.g., U.S. Pat. No. 6,761, 741, ibid., which is incorporated herein by reference).

Actuated fluid deflector structures are formed at the boundaries of the femoral component and the acetabular component. The fluid deflector structures are configured to deflect synovial fluid flow and associated debris particles away from the interfaces between the prosthesis components and bone and to mitigate transient joint fluid pressure on the prosthesis-bone interfaces during physiological use of the joint. The fluid deflector structures are also configured to capture debris particles in the joint fluid, thus reducing the likelihood of periprosthetic bone resorption and artificial joint loosening (see e.g., Fahlgren et al., ibid., which is incorporated herein by reference).

The artificial joint is fabricated using processes of investment casting, milling and compression molding. For example, a solid model comprised of a thermally labile material (e.g., wax) is made by injection molding and then a ceramic shell is created by coating the solid wax model. The ceramic shell is recovered after melting the solid model and used as a mold to cast the components of the prosthesis. See e.g., U.S. Pat. No. 5,665,118, ibid., which is incorporated herein by reference. A series of cavities are cast around the circumference of the femoral component and at the base of the neck of the acetabular component, with associated apertures within non-contact surfaces of the prosthesis. These cavities are configured to contain actuated fluid deflector structures with size, shape, number and position as required by the specific prosthesis design.

Magnetic actuated fluid deflector structures are constructed from polydimethylsiloxane (PDMS, available from Dow Corning Corp., Midland, Mich.) containing permanently magnetic nanoparticles. Carbon coated iron particles approximately 70 nm in diameter (available from M K Impex Corp., Missisauga, ON, Canada) are dispersed in PDMS to form a composite. This composite is then cast in the cavities of the femoral and acetabular components to form fluid deflector structures approximately 1 cm long and 3 mm wide protruding from the cavities (see e.g., van Engen, ibid., which is incorporated herein by reference). Each fluid deflector structure includes a proximal end that is positioned within the associated cavity, the proximal end of a size and shape to be blocked from leaving the cavity by the size and shape of the associated aperture. Each fluid deflector structure includes a region traversing the aperture. Each fluid deflector structure also includes a functional region approximately 1 cm long and 3 mm wide external to the cavity and aperture. The fluid deflector structures are magnetized by repeated movement of a permanent magnet along the long axis of the deflectors with a magnetic field of about 500 mTesla. The fluid deflector structures also include distal edge regions which contain adhesive tips configured to capture and retain debris particles. Artificial actuated cilia which adhere to particles and are used for propelling particles (antifouling) and trapping particles (filtration) are described (see e.g., Bhattacharya et al., "Propulsion and Trapping of Microparticles by Active Cilia Arrays," *Langmuir* 28: 3217-3226, (2012) which is incorporated herein by reference).

A permanent magnet is constructed in the neck of the femoral component to actuate the magnetic fluid deflector structures with a magnetic field that is oriented substantially perpendicular to the deflectors. A permanent magnet with a magnetic field of approximately 500 mTesla is placed in the neck region of the femoral component to actuate the magnetic fluid deflector structures on the femoral and acetabular components as the hip joint moves. For example, a magnetic field of approximately 50 mTesla applied perpendicular to magnetic cilia has been shown to cause a deflection of approximately 0.5 millimeter (see van Engen, ibid., which is incorporated herein by reference). See also US Patent Application No. 2006/0149386, "Joint Prosthesis," to Clarke and Lee, which is incorporated by reference herein.

Magnetic fluid deflector structures with distal edge regions that contain adhesive tips are positioned around the circumference of the femoral stem and the acetabular cup. The position, size, shape, number and orientation of the fluid deflector structures on each prosthesis component is configured to divert synovial joint fluid and associated debris particles away from the bone-prosthesis interfaces. Each of the fluid deflector structures is also configured to trap debris particles from synovial joint fluid with the adhesive tips attached to the distal edge regions of the fluid deflector structures. Models to calculate the optimal adhesive force and stiffness for the fluid deflector structures to trap particles are described (see Bhattacharya et al., ibid., which is incorporated herein by reference). Actuated magnetic fluid deflector structures with distal edge regions that contain adhesive tips are configured to move in response to the motion of a magnet positioned within the femoral component. Physiological movement of the artificial hip joint moves the magnet within the femoral stem into proximity of the fluid deflector structures and causes the fluid deflector structures to bend or flex in response to the magnetic field. Movement of the fluid deflector structures promotes directed fluid flow and trapping of debris particles (see e.g., van Engen, ibid. and Bhattacharya et al., ibid., which are each incorporated herein by reference). Repeated "beating" of the fluid deflector structures during regular activities, e.g., walking, running, sitting, reclining, or sleeping, acts to divert the flow of synovial fluid away from the prosthesis-bone interfaces and traps debris particles within the fluid with the adhesive tips at the distal edge regions of the fluid deflector structures. Thus, the artificial hip joint with actuated adhesive fluid deflector structures reduces the likelihood of osteolysis, periprosthetic bone resorption and prosthesis loosening in vivo.

Example 5

An Artificial Hip Joint Including Fluid Deflector Structures Configured to Respond to a Magnetic Field A hip joint prosthesis is fabricated with actuated fluid deflector structures on select non-contact surfaces of the device. The actuated fluid deflector structures are configured to divert joint fluid and debris particles away from the interface regions between the implanted artificial joint and the patient's bones. Debris particles within the joint fluid are associated with an increased likelihood of osteolysis and aseptic loosening of the prosthetic implant.

The hip joint prosthesis includes a femoral component which includes a head (or ball), a neck, and a stem which is configured to be implanted in the medullary canal of the femur. The hip joint prosthesis also includes an acetabular component that includes an outer and inner cup, with the outer cup configured to be attached to pelvic bone and the inner cup forming a socket that bears the head of the femoral component in vivo. The neck and stem of the femoral component are predominately fabricated from titanium (see e.g., U.S. Pat. No. 6,761,741, ibid., which is incorporated herein by reference).

The artificial joint is fabricated using processes of investment casting, milling and compression molding. For example, a solid model comprised of a thermally labile material (e.g., wax) is made by injection molding and then a ceramic shell is created by coating the solid wax model. The ceramic shell is recovered after melting the solid model and used as a mold to cast the components of the prosthesis. See e.g., U.S. Pat. No. 5,665,118, ibid., which is incorporated herein by reference. A series of cavities are cast around the circumference of the acetabular cup, with associated apertures within non-contact surfaces of the prosthesis. The cavities in the acetabular cup are configured with substantially circular sides, to contain substantially circular mechanisms attached to fluid deflector structures, of size, shape, number and position as required by the specific prosthesis design.

Figure 11:
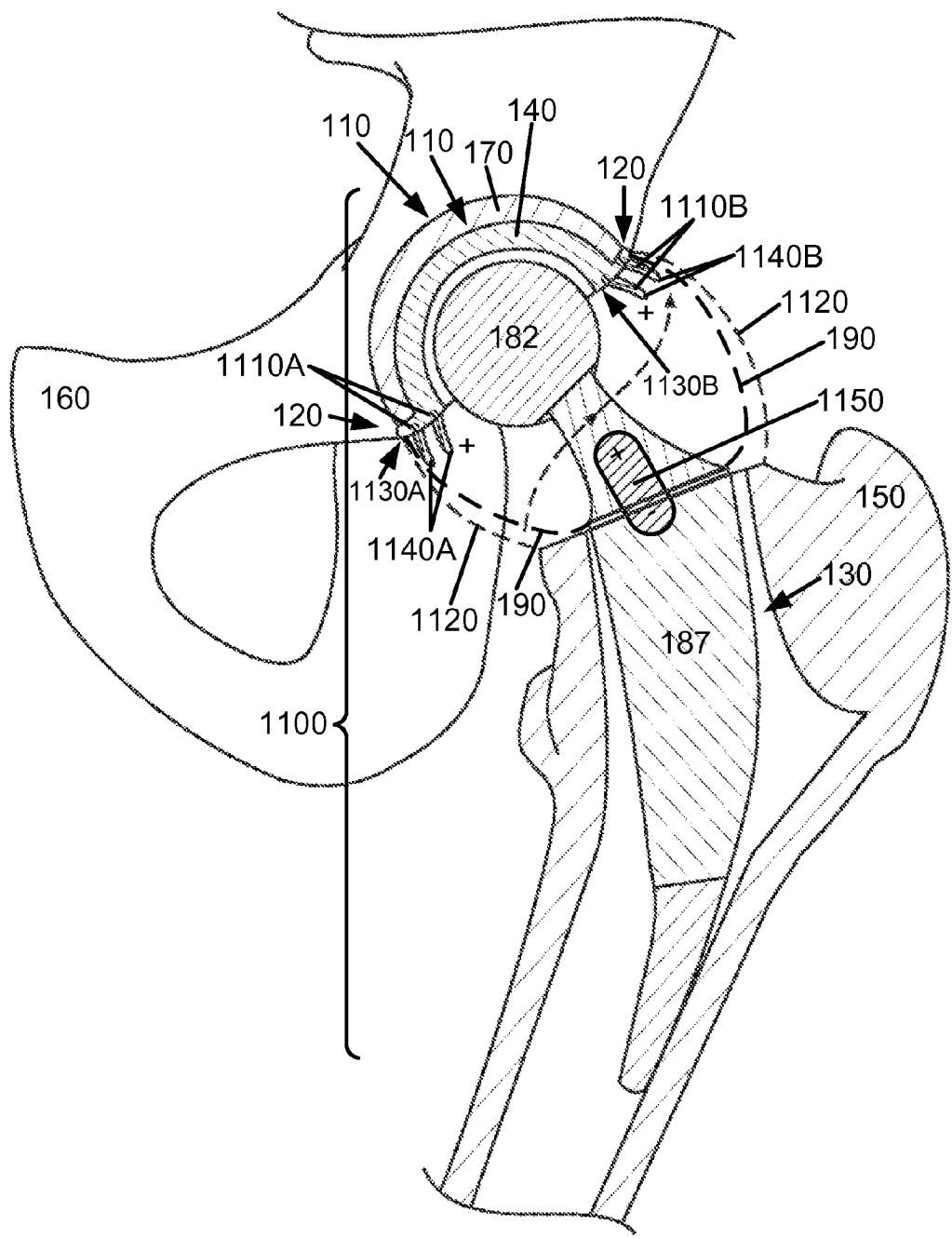
FIG. 11 depicts an artificial hip joint in cross-section.

A permanent magnet is constructed in the neck of the femoral component, with a magnetic field that is oriented substantially along the long axis of the neck of the femoral component. FIG. 11 illustrates the permanent magnet 1100 embedded within the femoral stem component 187, with the axis of polarity of the magnet (represented as + and − in the Figure) oriented substantially along the long axis of the femoral stem component 187. A permanent magnet with a magnetic field of approximately 500 mTesla is placed in the neck region of the femoral component to actuate the magnetic fluid deflector structures on the acetabular cup that approach the permanent magnet 1100 as the hip joint moves. For example, a magnetic field of approximately 50 mTesla applied perpendicular to magnetic cilia has been shown to cause a deflection of approximately 0.5 millimeter (see van Engen, ibid., which is incorporated herein by reference). See also US Patent Application No. 2006/0149386, "Joint Prosthesis," to Clarke and Lee, which is incorporated by reference herein.

As illustrated in FIG. 11, each of the fluid deflecting structures 140A, 140B is attached to a mechanism 1110A, 1110B that includes a ball-like end configured to fit within the cavities in the acetabular cup, and an attached rod projecting away from the non-contact surface of the prosthesis along the long axis of the fluid deflecting structures 140A, 140B. The ball-like end of the mechanism 1110A, 1110B is of a size and shape configured to fit within a corresponding cavity in the femoral stem component 187, and to rotate within the cavity. Each of the rod structures of the mechanism 1110A, 1110B is a permanent magnet, with an axis of polarity along the long axis of the rod. The polarity of the distal end of the rod structure of a mechanism 1110A, 1110B is the same as the polarity of the closer end of the permanent magnet 1100 embedded within the femoral stem component 187. For example, FIG. 11 illustrates a permanent magnet 1100 embedded within the femoral stem component 187 with a "north" polar end ("+") at the end of the permanent magnet 1100 adjacent to the femoral ball 182. Correspondingly, FIG. 11 shows the distal ends of the rod structures of the mechanisms 1110A, 1110B as including a "north" polar end ("+"). Although the instant illustration shows these ends as including a "north" polar end ("+"), embodiments also include those with corresponding "south" polar ends ("−") on the end of the permanent magnet 1100 adjacent to the femoral ball 182 and the distal ends of the rod structures of the mechanisms 1110A, 1110B.

Actuated fluid deflector structures 140A, 140B are formed at the edge region of the acetabular liner. The fluid deflector structures are configured to deflect synovial fluid flow and associated debris particles away from the interfaces between the prosthesis components and bone and to mitigate transient joint fluid pressure on the prosthesis-bone interfaces during physiological use of the joint. Magnetic actuated fluid deflector structures are constructed from polydimethylsiloxane (PDMS, available from Dow Corning Corp., Midland, Mich.) around the core rods of the mechanism 1110A, 1110B. The PDMS is cast around the rod structures of the mechanisms 1110A, 1110B to form fluid deflector structures approximately 10 mm long and 3 mm wide protruding from the cavities (see e.g., van Engen, ibid., which is incorporated herein by reference). Each fluid deflector structure 140A, 140B includes a mechanism 1110A, 1110B including a rod structure with a proximal end that is positioned within the associated cavity, the proximal end of a size and shape to be blocked from leaving the cavity by the size and shape of the associated aperture while allowing for rotation within the cavity. Each fluid deflector structure 140A, 140B includes a region traversing the aperture. Each fluid deflector structure 140A, 140B also includes a functional deflector region approximately 10 mm long and 3 mm wide external to the cavity and aperture.

Magnetic fluid deflector structures 140A, 140B are positioned around the circumference of the acetabular cup 175. The position, size, shape, number and orientation of the fluid deflector structures 140A, 140B is configured to divert synovial joint fluid and associated debris particles away from the bone-prosthesis interfaces. Actuated magnetic fluid deflector structures 140A, 140B are configured to move in response to the motion of the magnet 1100 positioned within the femoral stem component 187. Physiological movement of the artificial hip joint moves the magnet 1100 within the femoral stem 187 into proximity of the fluid deflector structures 140A on the adjacent edge of the acetabular cup 175. The proximity of the same-polarity magnetic fields causes the fluid deflector structures 140A to bend or flex in response to the magnetic field in a direction away from the femoral stem 187. Movement of the fluid deflector structures 140A promotes directed fluid flow away from the bone-prosthesis interface. Repeated "beating" of the fluid deflector structures 140A, 140 B in response to the relative re-positioning of the fluid deflector structures 140A, 140 B and the magnet 1100 positioned within the femoral stem component 187 during regular activities, e.g., walking, running, sitting, reclining, or sleeping, acts to divert the flow of synovial fluid away from the prosthesis-bone interfaces. Thus, the artificial hip joint with embedded magnet 1100 and actuated fluid deflector structures 140 A, 140 B reduces the likelihood of osteolysis, periprosthetic bone resorption and prosthesis loosening in vivo.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An artificial joint prosthesis, comprising:
    a bone-facing surface of an artificial joint prosthesis, the bone-facing surface configured to face a bone-prosthesis interface in vivo;
    a first structural component of the artificial joint prosthesis including a load-bearing surface of the artificial joint prosthesis, the first structural component fabricated from at least one polymer and a plurality of magnetic particles arranged as a magnetic polymer nanocomposite material; and
    a second structural component of the artificial joint prosthesis including at least one magnet configured to create a magnetic field within the artificial joint, the at least one magnet positioned to form a magnetic field directed to influence a location of debris including the magnetic particles in the joint to a position distinct from the bone-prosthesis interface in vivo.

2. An artificial joint prosthesis, comprising:
    a bone-facing surface of an artificial joint prosthesis, the bone-facing surface configured to face a bone-prosthesis interface in vivo;
    a first component of the artificial joint prosthesis including a contact surface of the artificial joint prosthesis, the first component fabricated from at least one polymer including a plurality of magnetic particles embedded in a polymer matrix; and
    a second component of the artificial joint prosthesis including at least one magnet configured to create a magnetic field within the artificial joint, the at least one magnet positioned to form a magnetic field directed to influence a location of debris including the magnetic particles in the joint to a position distinct from the bone-prosthesis interface in vivo.

3. The artificial joint prosthesis of claim 2, wherein the artificial joint prosthesis comprises at least one of:
a hip joint prosthesis, a knee joint prosthesis, a shoulder joint prosthesis, an ankle joint prosthesis, or an elbow joint prosthesis.

4. The artificial joint prosthesis of claim 2, wherein the polymer includes polyethylene.

5. The artificial joint prosthesis of claim 2, wherein the first component comprises:
one or more indentations at the contact surface.

6. The artificial joint prosthesis of claim 2, wherein the second component is fabricated with an interior region proximal to the contact surface of the joint, the interior including at least one magnet and an exterior region distal to the joint, the exterior region including magnetic shielding.

7. The artificial joint prosthesis of claim 2, comprising:
at least one fluid deflecting structure attached to a non-contact surface of the artificial joint.

8. The artificial joint prosthesis of claim 2, comprising:
at least one particle retaining structure attached to at least one non-contact surface of the artificial joint, the at least one particle retaining structure positioned in a location to retain the debris including the magnetic particles influenced by the magnetic field.

9. An artificial hip joint prosthesis, comprising:
a bone-facing surface of an artificial hip joint prosthesis, the bone-facing surface configured to face a bone-prosthesis interface in vivo;
a first component of the artificial hip joint prosthesis including a contact surface of the artificial hip joint prosthesis, the first component fabricated from at least one polymer including a plurality of magnetic particles embedded in a polymer matrix; and
a second component of the artificial hip joint prosthesis including at least one magnet configured to create a magnetic field within the artificial hip joint, the at least one magnet positioned to form a magnetic field directed to influence a location of debris including the magnetic particles in the joint to a position distinct from the bone-prosthesis interface in vivo.

10. The artificial hip joint prosthesis of claim 9, wherein the polymer includes polyethylene.

11. The artificial hip joint prosthesis of claim 9, wherein the first component comprises:
one or more indentations at the contact surface.

12. The artificial hip joint prosthesis of claim 9, wherein the second component is fabricated with an interior region proximal to the contact surface of the hip joint, the interior including at least one magnet and an exterior region distal to the hip joint, the exterior region including magnetic shielding.

13. The artificial hip joint prosthesis of claim 9, wherein the second component comprises:
at least one permanent magnet.

14. The artificial hip joint prosthesis of claim 9, wherein the second component comprises:
at least one electromagnet.

15. The artificial hip joint prosthesis of claim 9, comprising:
at least one fluid deflecting structure attached to a non-contact surface of the artificial hip joint.

16. The artificial hip joint prosthesis of claim 9, comprising:
at least one particle retaining structure attached to at least one non-contact surface of the artificial hip joint, the at least one particle retaining structure positioned in a location to retain the debris including the magnetic particles influenced by the magnetic field.

17. The artificial hip joint prosthesis of claim 9, comprising:
a particle retaining structure including a first edge region, the first edge region attached to at least one non-contact surface a first component of the artificial hip joint; and
the particle retaining structure including a second edge region, the second edge region attached to at least one non-contact surface of a second component of the artificial hip joint.

18. An artificial knee joint prosthesis, comprising:
a bone-facing surface of an artificial knee joint prosthesis, the bone-facing surface configured to face a bone-prosthesis interface in vivo;
a first component of the artificial knee joint prosthesis including a contact surface of the artificial knee joint prosthesis, the first component fabricated from at least one polymer including a plurality of magnetic particles embedded in a polymer matrix; and
a second component of the artificial knee joint prosthesis including at least one magnet configured to create a magnetic field within the artificial knee joint, the at least one magnet positioned to form a magnetic field directed to influence a location of debris including the magnetic particles in the joint to a position distinct from the bone-prosthesis interface in vivo.

19. The artificial knee joint prosthesis of claim 18, wherein the polymer includes polyethylene.

20. The artificial knee joint prosthesis of claim 18, wherein the first component comprises:
one or more indentations at the contact surface.

21. The artificial knee joint prosthesis of claim 18, wherein the second component is fabricated with an interior region proximal to the contact surface of the knee joint, the interior including at least one magnet and an exterior region distal to the knee joint, the exterior region including magnetic shielding.

22. The artificial knee joint prosthesis of claim 18, wherein the second component comprises:
at least one permanent magnet.

23. The artificial knee joint prosthesis of claim 18, wherein the second component comprises:
at least one electromagnet.

24. The artificial knee joint prosthesis of claim 18, comprising:
at least one fluid deflecting structure attached to a non-contact surface of the artificial knee joint.

25. The artificial knee joint prosthesis of claim 18, comprising:
at least one particle retaining structure attached to at least one non-contact surface of the artificial knee joint, the at least one particle retaining structure positioned in a location to retain the debris including the magnetic particles influenced by the magnetic field.

26. The artificial knee joint prosthesis of claim 18, comprising:
a particle retaining structure including a first edge region, the first edge region attached to at least one non-contact surface a first component of the artificial knee joint; and
the particle retaining structure including a second edge region, the second edge region attached to at least one non-contact surface of a second component of the artificial knee joint.

27. An artificial shoulder joint prosthesis, comprising:
a bone-facing surface of an artificial shoulder joint prosthesis, the bone-facing surface configured to face a bone-prosthesis interface in vivo;

a first component of the artificial shoulder joint prosthesis including a contact surface of the artificial shoulder joint prosthesis, the first component fabricated from at least one polymer including a plurality of magnetic particles embedded in a polymer matrix; and a second component of the artificial shoulder joint prosthesis including at least one magnet configured to create a magnetic field within the artificial shoulder joint, the at least one magnet positioned to form a magnetic field directed to influence a location of debris including the magnetic particles in the joint to a position distinct from the bone-prosthesis interface in vivo.

28. The artificial shoulder joint prosthesis of claim 27, wherein the polymer includes polyethylene.

29. The artificial shoulder joint prosthesis of claim 27, wherein the first component comprises:

one or more indentations at the contact surface.

30. The artificial shoulder joint prosthesis of claim 27, wherein the second component is fabricated with an interior region proximal to the contact surface of the shoulder joint, the interior including at least one magnet and an exterior region distal to the joint, the exterior region including magnetic shielding.

31. The artificial shoulder joint prosthesis of claim 27, wherein the second component comprises:

at least one permanent magnet.

32. The artificial shoulder joint prosthesis of claim 27, wherein the second component comprises:

at least one electromagnet.

33. The artificial shoulder joint prosthesis of claim 27, comprising:

at least one fluid deflecting structure attached to a non-contact surface of the artificial shoulder joint.

34. The artificial shoulder joint prosthesis of claim 27, comprising:

at least one particle retaining structure attached to at least one non-contact surface of the artificial shoulder joint, the at least one particle retaining structure positioned in a location to retain the debris including the magnetic particles influenced by the magnetic field.

35. The artificial shoulder joint prosthesis of claim 27, comprising:

a particle retaining structure including a first edge region, the first edge region attached to at least one non-contact surface of a first component of the artificial shoulder joint; and the particle retaining structure including a second edge region, the second edge region attached to at least one non-contact surface of a second component of the artificial shoulder joint.

* * * * *

UNITED STATES PATENT AND TRADEMARK OFFICE
CERTIFICATE OF CORRECTION

PATENT NO. : 8,845,741 B2  
APPLICATION NO. : 13/675068  
DATED : September 30, 2014  
INVENTOR(S) : Edward S. Boyden et al.

Page 1 of 1

It is certified that error appears in the above-identified patent and that said Letters Patent is hereby corrected as shown below:

On the title page item 73 Assignee:
"Seavete LLC" should read --Elwha LLC--

Signed and Sealed this  
Thirty-first Day of May, 2016

Michelle K. Lee  
*Director of the United States Patent and Trademark Office*